United States Patent
Howard et al.

(10) Patent No.: US 9,650,416 B2
(45) Date of Patent: May 16, 2017

(54) αVβ6 PEPTIDE LIGANDS AND THEIR USES

(71) Applicant: Cancer Research Technology Limited, London (GB)

(72) Inventors: Mark J. Howard, Kent (GB); Danielle Dicara, San Francisco, CA (US); John Marshall, London (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 14/567,274

(22) Filed: Dec. 11, 2014

(65) Prior Publication Data

US 2015/0125392 A1     May 7, 2015

Related U.S. Application Data

(60) Division of application No. 13/743,714, filed on Jan. 17, 2013, now Pat. No. 8,927,501, which is a continuation of application No. 12/088,998, filed as application No. PCT/GB2006/003673 on Oct. 3, 2006, now Pat. No. 8,383,593.

(30) Foreign Application Priority Data

Oct. 3, 2005  (GB) ................... 0520068.8

(51) Int. Cl.
*C07K 7/06* (2006.01)
*C07K 7/08* (2006.01)
*A61K 49/00* (2006.01)

(52) U.S. Cl.
CPC ........... *C07K 7/06* (2013.01); *A61K 49/00* (2013.01); *C07K 7/08* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 8,383,593 B2 | 2/2013 | Howard et al. | |
| 8,927,501 B2 | 1/2015 | Howard et al. | |
| 2003/0176315 A1 | 9/2003 | Barry et al. | |

FOREIGN PATENT DOCUMENTS

| | | |
|---|---|---|
| AU | 772782 | 2/2001 |
| CA | 2355874 | 6/2000 |
| CA | 2377224 | 1/2001 |
| CA | 2379022 | 1/2001 |
| EP | 0 114 759 | 8/1984 |
| WO | 9523166 | 8/1995 |

OTHER PUBLICATIONS

Hammen P.K., The role of positive charges and structural segments in the presequence of rat liver aldehyde dehydrogenase in import into mitochondria, J Biol Chem. Aug. 30, 1996;271(35):21041-8.*
Jackson, T. "The Epithelial Integrin αvβ6 is a Receptor for Foot-and-Mouth Disease Virus," J Virol. Jun. 2000; 74(11): 4949-4956.*
Aoki, Y., et al Potential tumor-targeting peptide vector of histidylated oligolysine conjugated to a tumor-homing RGD motif, Cancer Gene Therapy (2001) 8, 783-787.*
Ogawa, M., Direct electrophilic radiofluorination of a cyclic RGD peptide for in vivo αvβ3 integrin related tumor imaging, Nuclear Medicine and Biology 30 (2003) 1-9.*
Nomenclature and Symbolism for Amino Acids and Peptides Pure & Appi. Chem., vol. 56, No. 5, pp. 595-624, 1984.*
Ravindra Acharya et al., "The three-dimensional structure of foot-and-mouth disease virus at 2.9 A resolution", Nature, 337(23): 709-716 (1989).
Justin P. Annes et al., "The integrin αvβ6 binds and activates latent TGFβ3", FEBS Letters, 511: 65-68 (2002).
Barry Baxt et al., "The Effect of Peptides Containing the Arginine-Glycine-Aspartic Acid Sequence on the Adsorption of Foot-and-Mouth Virus to Tissue Culture Cells", Virus Genes, 4(1): 73-83 (1990).
Alison Burman et al., "Specificity of the VP1 GH Loop of Foot-and-Mouth Disease Virus for αv Integrins", J Virology, 80(19): 9798-9810 (2006).
Danielle Dicara et al., "Foot-and-Mouth Disease Virus Forms a Highly Stable, EDTA-Resistant Complex with Its Principal Receptor, Integrin αvβ6: Implications for Infectiousness", J. Virology,, 82(3): 1537-1546 (2008).
Danielle Dicara et al., "Structure-Function Analysis of Arg-Gly-Asp Helix Motifs in αvβ6 Integrin Ligands", J. Biol. Chem., 282(13) 9657-9665 (2007).
Simon L. Goodman et al., "Nanomolar Small Molecule Inhibitors for αvβ5 and αvβ3 Integrins", J. Med. Chem., 45: 1045-1051 (2002).
Terry Jackson et al., "The Epithelial Integrin αvβ6 is a Receptor for Foot-and-Mouth Disease Virus", J. Virology, 74(11): 4949-4956 (2000).
Ht. Liebertman et al., "RGD-Containing Peptides of VP1 of Foot-and-Mouth Disease Virus (FMDV) Prevent Virus Infection in Vitro", Acta. virol., 35: 90-93 (1991).

(Continued)

*Primary Examiner* — Thomas S Heard
(74) *Attorney, Agent, or Firm* — Patrick J. Hagan; Dann, Dorfman, Herrell and Skillman

(57) ABSTRACT

AVβ6 peptide ligands, functional variants thereof and their nucleic acids encoding them are disclosed with their uses in the treatment and imaging of AVβ6 mediated diseases.

15 Claims, 10 Drawing Sheets

(56) References Cited

OTHER PUBLICATIONS

Derek Logan et al., "Structure of a major immunogenic site on foot-and-mouth disease virus", Nature, 362 (566-568 (1993).

Mauricio G. Mateu et al., "Systematic Replacement of Amino Acid Residues within an Arg-Gly-Asp-containing Loop of Foot-and-Mouth Disease Virus and Effect on Cell Recognition", J. Biol. Chem., 271(22): 12814-12819 (1996).

Paul Monaghan et al., "The αvβ6 integrin receptor for Foot-and-mouth disease virus is expressed constitutively on the epithelial cells targeted in cattle", J. General Virology, 86: 2769-2780 (2005).

John S. Munger et al., "The Integrin αvβ6 Binds and Activates Latent TGFβ1: A Mechanism for Regulating Pulmonary Inflammation and Fibrosis", Cell, 96: 319-328 (1999).

Masanobu Obara et al., "Site-Directed Mutagenesis of the Cell-Binding Domain of Human Fibronectin: Separable, Synergistic Sites Mediate Adhesive Function", Cell, 53: 649-657 (1988).

Wendy F. Ochoa et al., "A multiply substituted G-H loop from foot-and-mouth disease virus in complex with a neutralizing antibody: a role for water molecules", J. Gen. Virol., 81: 1495-1505 (2000).

Erkki Ruoslahti, "RGD and Other Recognition Sequences for Integrins", Annu. Rev. Cell Dev. Biol., 12: 697-715 (1996).

Alu Surovoi et al., "Is the Arg-Gly-Asp sequence the site for foot-and-mouth disease virus binding with cell receptor?", Bioorg. Khim., 14(7): 965-8 (1988) [Abstract].

Gordon C. Tucker et al., "αv Integrin Inhibitors and cancer therapy", Curr. Opin Investig. Drugs, 4(6): 722-731 (2003).

Nuria Verdaguer et al., "Structure of the major antigenic loop of foot-and-mouth disease virus complexed with a neutralizing antibody: direct involvement of the Arg-Gly-Asp motif in the interaction".

Nuria Verdaguer et al., "A Similar Pattern of Interaction for Different Antibodies with a Major Antigenic Site of Foot-and-Mouth Disease Virus: Implications for Intratypic Antigenic Variation", J. Virol., 72(1): 739-748 (1998).

Nuria Verdaguer et al., "Flexibility of the Major Antigenic Loop of Foot-and-Mouth Disease Virus Bound to a Fab Fragment of a Neutralising Antibody: Structure and Neutralisation", 255: 260-266 (1999).

Ann Weinacker et al., "Role of the Integrin αvβ6 in Cell Attachment to Fibronectin", J. Biol. Chem., 269(9): 6940-6948 (1994).

Jian-Pong Xiong et al., "Crystal Structure of the Extracellular Segment of Integrin αvβ3 in Complex with an Arg-Gly-Asp Ligand", Science, 296: 151-155 (2002).

Pfaff et al., "Analysis of Neutralizing Epitopes on Foot-and-Mouth Disease Virus", J. Virol, 62: 2033-2040 (1988).

Kraft, S. et al., "Definition of an Unexpected Ligand Recognition Motif for αβ6Integrin", J. Biol. Chem., 274(4): 1979-1985 (1999).

Jackson, T. et al., "Arginine-Glycine-Aspartic Acid-Specific Binding by Foot-and-Mouth Disease Viruses to the Purified Integrin αβ3 In Vitro", J. Virology, 71(11): 8357-8361 (1997).

Valero, Mari-Luz et al., "Native-like cyclic peptide models of a viral antigenic site: finding a balance between rigidity and flexibility", Journal of Molecular Recognition, 13: 5-13 (2000).

\* cited by examiner

Figure 9

αVβ6 PEPTIDE LIGANDS AND THEIR USES

CROSS-REFERENCE TO RELATED APPLICATIONS

This application is a divisional of U.S. patent application Ser. No. 13/743,714, filed Jan. 17, 2013, which is a continuation of U.S. patent application Ser. No. 12/088,998, filed Nov. 25, 2008 (now U.S. Pat. No. 8,383,593), which is the U.S. National Stage of International Application No. PCT/GB2006/003673, filed Oct. 3, 2006 which claims priority from United Kingdom Application No. 0520068.8, filed Oct. 3, 2005. The entire disclosure of each of the aforesaid applications is incorporated by reference in the present application.

FIELD OF THE INVENTION

The present invention relates to αvβ6 peptide ligands, functional variants thereof and their nucleic acids encoding them and their uses in the treatment and imaging of αvβ6 mediated diseases.

BACKGROUND OF THE INVENTION

Integrins are a large family of cell-surface receptors responsible for mediating cell-cell and cells-to-extracellular-matrix (ECM) adhesion. There are at least 24 different integrins, each a heterodimer composed of an α and β subunit, whose expression is determined by several factors including tissue, stage of development, and various tissue pathologies such as inflammation and cancer. Although they do not possess any intrinsic enzymatic activity themselves, subsequent to ligand binding, integrins translate extracellular cues into intracellular signals by bringing into juxtaposition a complex of cytoplasmic structural and signalling molecules that then interact and determine the cell response. As integrins are involved in most elements of cell behaviour including motility, proliferation, invasion and survival their roles in disease have been widely reported. In fact, some integrins are thought to play an active role in promoting certain diseases including cancer. For example αvβ3 has been implicated in promoting the invasive phenotype of melanoma and glioblastoma, owing to its multiple abilities including upregulating pro-invasive metalloproteinases as well as providing pro-migratory and survival signals. As integrin αvβ3 also is upregulated on endothelial cells of angiogenic blood vessels and may provide similar signals for the development of neo-vessels in cancer, such data have led many pharmaceutical and academic centres to develop antagonists of αvβ3 for therapeutic purposes many of which have been peptides or peptidomimetics. Thus, understanding the structural basis of integrin-ligand interaction would aid design of improved integrin antagonists.

αvβ6 is expressed only on epithelial cells. This integrin is involved in both normal and pathological tissue processes. Thus αvβ6 is upregulated by epithelial cells during wound healing and inflammation. It is likely that the ability of αvβ6 to locally activate TGFβ by binding to its protective propeptide, the latency associated peptide (LAP), explains the function of αvβ6 in these transient pathologies. Thus TGFβ can suppress inflammatory responses and epithelial proliferation suggesting that αvβ6 serves as a negative control to dampen-down these processes. However, chronic inflammation can lead to an excess of αvβ6-dependent activation of TGFβ resulting in fibrosis in the lung of experimental animals. It is likely that some pathologies that result in fibrosis in humans may also involve αvβ6-dependent TGFβ activation. Constitutive αvβ6 over-expression in the skin of mice resulted in chronic wounds appearing on a significant number of transgenic animals. Thus, chronic wounds associated with human diseases (e.g. certain forms of Epidermolysis Bullosa) may also promoted or exacerbated by upregulation of αvβ6 on the wound keratinocytes.

Recently, it has become clear that the integrin αvβ6 is a major new target in cancer. Although αvβ6 is epithelial-specific, it is weak or undetectable in most resting epithelial tissues but is strongly upregulated in many types of cancer, often at the invasive front. It has been shown that αvβ6 can promote carcinoma invasion by upregulating MMPs and promoting increased motility so that αvβ6 promotes survival of carcinoma cells by upregulating Akt. These data suggest strongly that αvβ6 is actively promoting the invasive phenotype. This suggestion is supported by the recent report showing that high expression of αvβ6 correlates with a significant reduction in median survival by colon cancer patients.

αvβ6 has been identified as a receptor for foot-and-mouth disease virus (FMDV) in vitro by binding through an RGD motif in the viral capsid protein, VP1.

SUMMARY OF THE INVENTION

The present invention arose from work directed to improving αvβ6-directed therapies, and more particularly to find novel binding ligands, for example which have an increased binding affinity and/or specificity improving the treatment and imaging of αvβ6 mediated diseases. These may have major benefits for patients with αvβ6 mediated diseases such as chronic fibrosis or carcinoma. In particular αvβ6 improved antagonists are highly in demand.

Broadly, the present invention is based on the surprising finding that the potency of peptide antagonists of αvβ6 depended on the presence of specific secondary structures in the peptide antagonists, and in particular peptides which comprise the sequence motif RGDLXXL/I (SEQ ID NO: 1/SEQ ID NO: 2), wherein LXXL/I is contained within an alpha helical structure. While crystal structure analysis of FMDV had previously shown that the RGD motif was comprised in a G-H lop of the VP1 capsid protein, which is at the tip of a hairpin turn followed by a $3_{10}$ helix, there was no indication that the position of the binding motif within a specific secondary structure was important for its binding potency. The present inventors found that the truncated peptides originating from the VP1 protein comprising the RGD motif showed increased binding potency and binding specificity. In particular, the binding specificity and the binding affinity increased with increasing helical propensity within the binding region of the peptide. Without being bound by theory it is thought that the α-helix structure within the LXXL motif of the αvβ6 binding peptide allows correct orientation of the RGDLXXL (SEQ ID NO: 1) motif to enable hydrophobic side chains to interact with a binding site on αvβ6. Moreover, the non-covalent contacts between residues in the helix and residues in the N-terminus stabilize the hairpin structure and thus present the RGD motif favourably for specific binding to αvβ6.

Accordingly, in a first aspect, the present invention provides a peptide comprising the sequence motif $RGDLX^5X^6L$ SEQ ID NO: 1) or $RGDLX^5X^6I$ (SEQ ID NO: 2), wherein $LX^5X^6L$ or $LX^5X^6I$ is contained within an alpha helical structure.

In a further aspect, the present invention provides an isolated nucleic acid molecule that encodes a peptide as defined herein, and an expression vector comprising the nucleic acid molecule.

In a further aspect, the present invention provides a peptide, nucleic acid molecule or expression vector as defined herein for use in therapy or diagnosis.

In a further aspect, the present invention provides a pharmaceutical composition peptide, nucleic acid molecule or expression vector as defined herein and a pharmaceutical acceptable carrier.

In a further aspect, the present invention provides a method of treating an αvβ6 mediated disease or a disease wherein cells overexpress αvβ6 comprising administering to a patient in need a therapeutically effective amount of a peptide, a nucleic acid molecule or an expression vector as defined herein.

In a further aspect, the present invention provides the use of a peptide, a nucleic acid molecule or an expression vector as defined herein for the preparation of a medicament for the treatment of an αvβ6 mediated disease or a disease wherein cells overexpress αvβ6. By way of example, these disease include chronic fibrosis, chronic obstructive pulmonary disease (COPD), lung emphysema, chronic wounding skin disease (e.g. epidermolysis bullosa) or cancer.

In a further aspect, the present invention provides a method of imaging epithelial cells in the body of an individual, the method comprising administering to the individual an effective amount of a peptide as defined herein and detecting presence of the peptide in the body.

In a further aspect, the present invention provides a method for the diagnosis or prognosis of an αvβ6 mediated disease, the method comprising administering to an individual an effective amount of a peptide as defined herein and detecting presence of the peptide in the body.

In a further aspect, the present invention provides a method of delivering a therapeutic active moiety to a αvβ6 expressing cell or a tissue containing αvβ6 expressing cells in a patient, the method comprising administering a peptide of the present invention.

In a further aspect, the present invention provides a method of improving the binding specificity of an αvβ6 binding peptide by increasing the alpha helical content of the peptide.

Embodiments of the present invention will now be further described by way of example and not limitation with reference to the accompanying figures and tables.

All chemical shifts are referenced externally to a 100 μM solution of dimethylsilapetane sulphonic acid (DSS) in PBS/30% (v/v) TFE.

Figure 5:
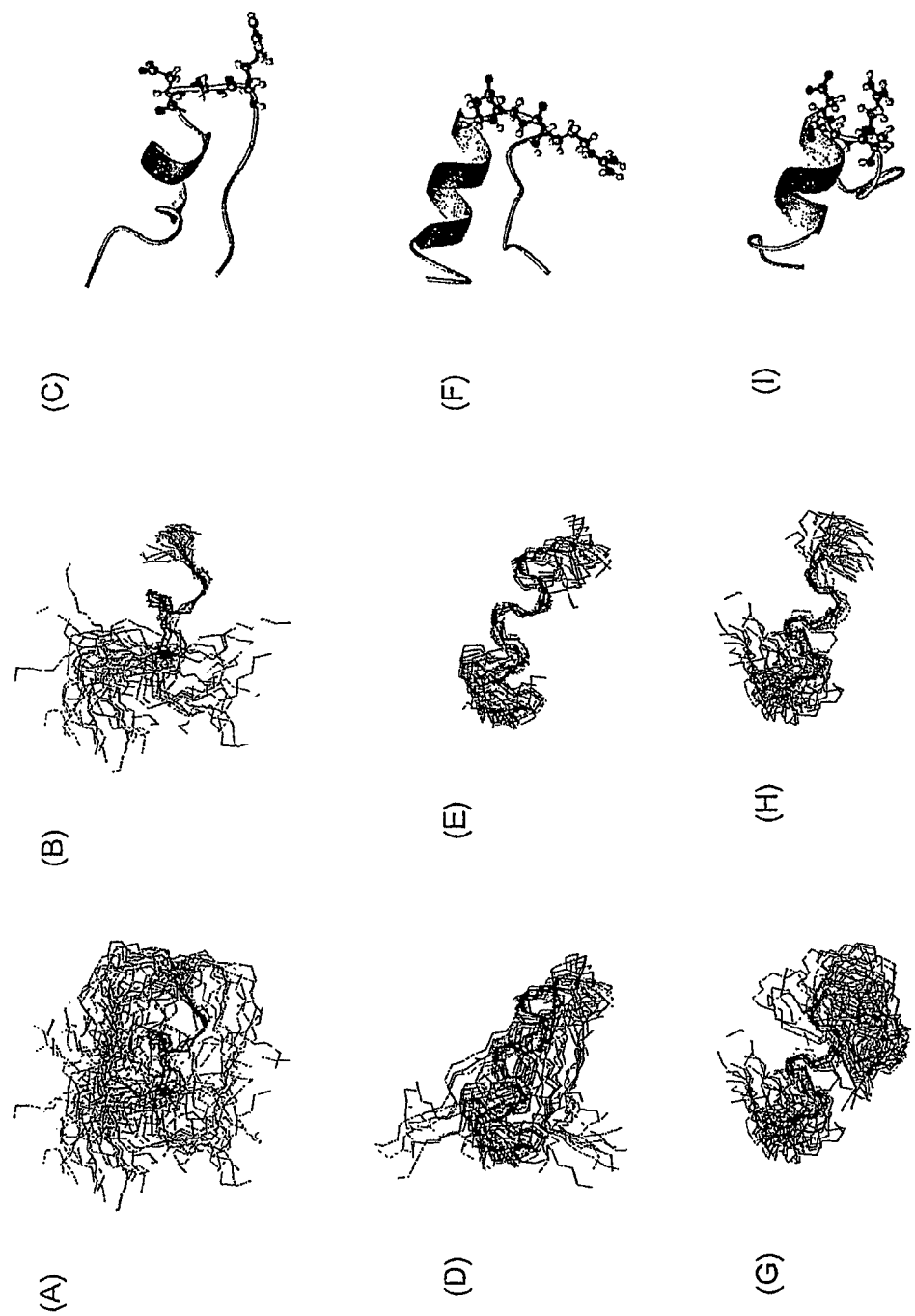

FIG. 5. Calculated structures for A20FMDV1: (a-c); A20FMDV2: (d-f) and A20LAP: (g-i). Ensembles of 40 structures (a), (d) and (e) show all backbone bonds (residues 1-20); ensembles of 40 structures (b), (e) and (h) show backbone bonds from GLXX to C-terminus to highlight the calculated convergence on each helix. The bonds coloured red identify the LXX[L/I]X×X region that was used to fit the ensembles and create data in Table 2. Ribbon diagrams (c), (f) and (i) are shown of the ensemble average structure for each peptide with the RGD motif shown in ball and stick. All figures were created in MOLMOL 2k.2 (Koradi et al, 1996).

Figure 6:
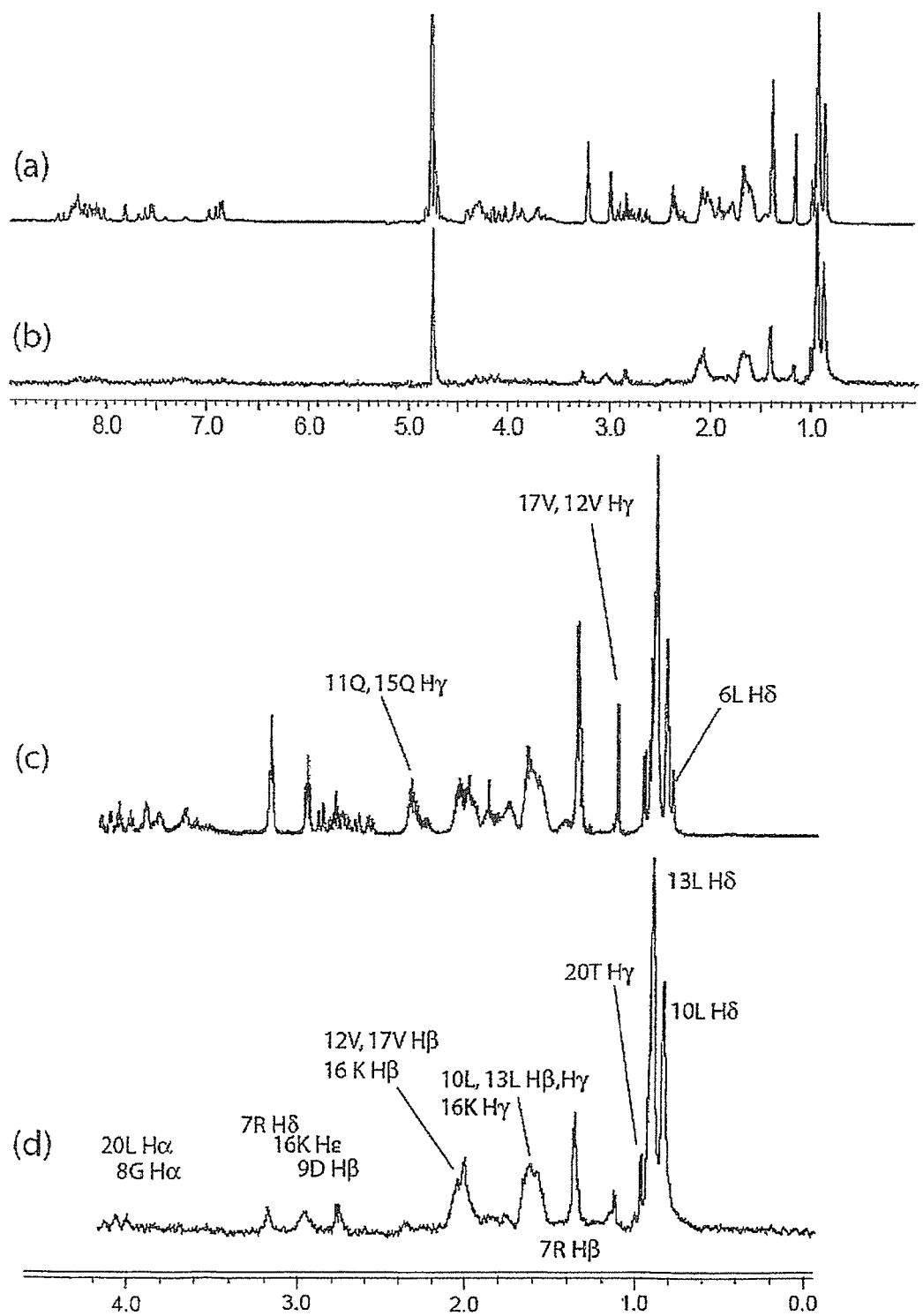

FIG. 6. 1H STD NMR spectra of integrin αvβ6 and peptide A20FMDV2 in the presence of $Ca^{2+}$ and $Mg^{2+}$. (a) and (c) are the control spectrum (no STD transfer showing peptide signals) whereas (b) and (d) are the STD difference spectrum with 30 ms spin-lock filter. Expansions (c) and (d) have key residue resonances highlighted in the data.

Figure 7:
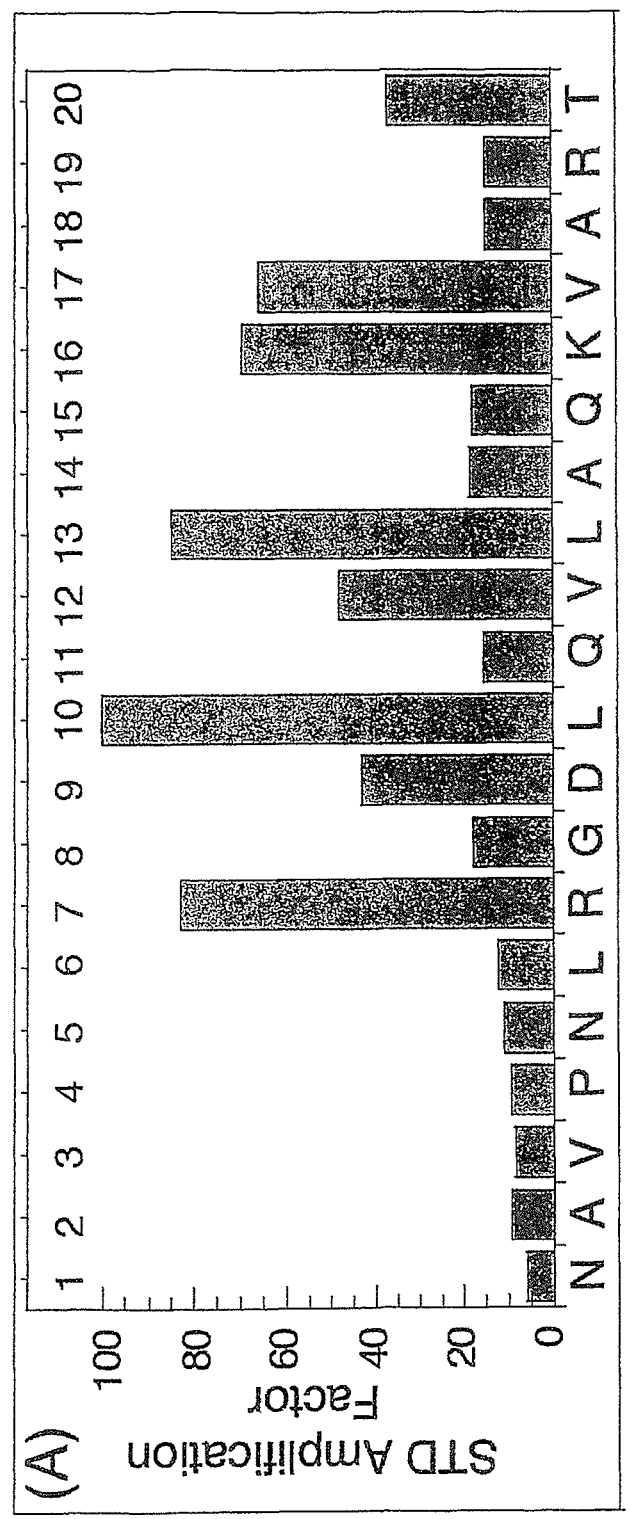

FIG. 7. The absolute STD NMR transfers in between integrin αvβ6 and A20FMDV2 (SEQ ID NO: 8) shown as a percentage on each amino acid peptide in the presence of $Ca^{2+}$ and $Mg^{2+}$.

Figure 8:
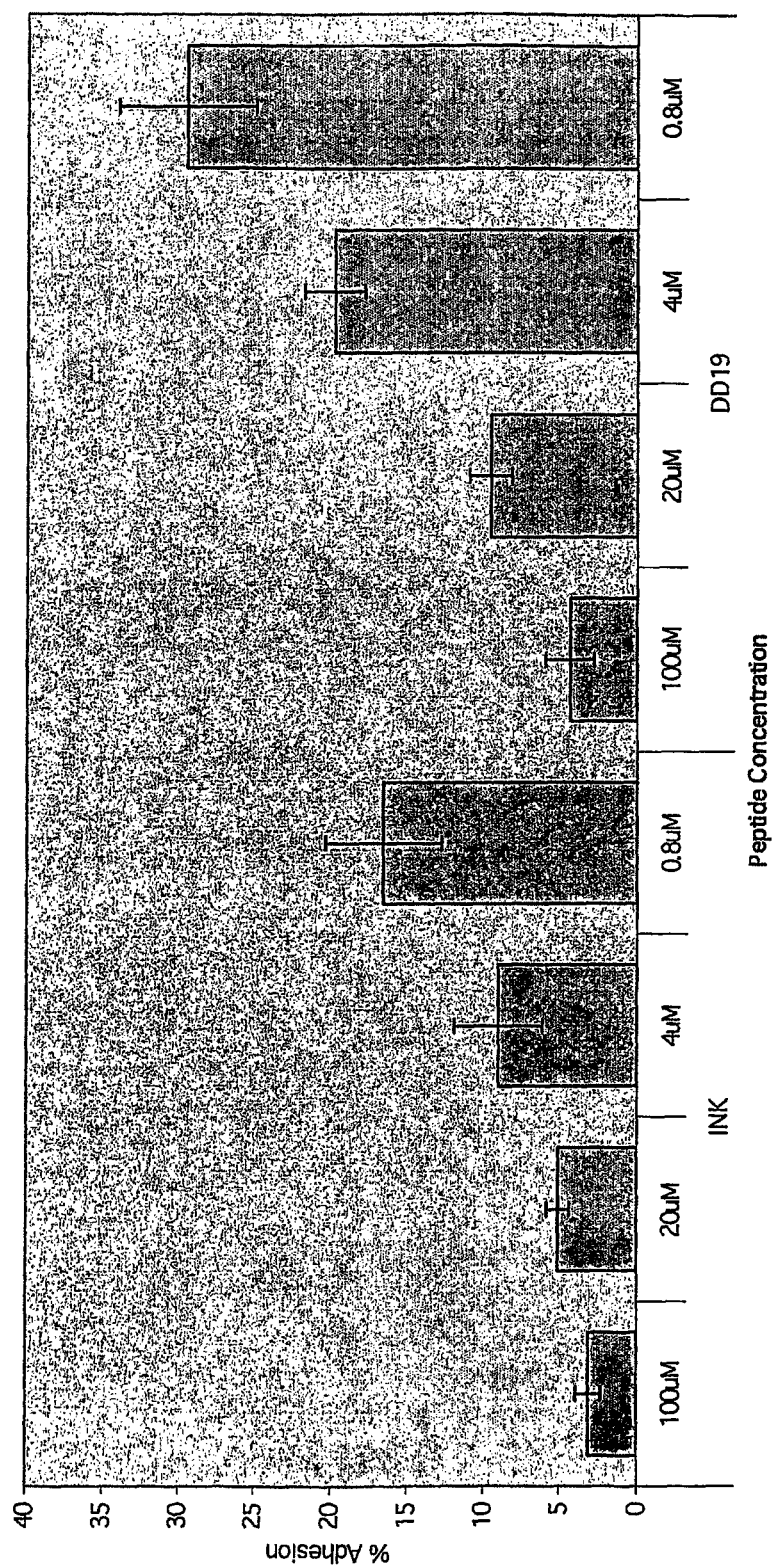

FIG. 8. Effect of INK and DD19 peptides on αvβ6-dependent adhesion of 3T3 B6.19 to LAP. Shown are the peptide concentration of both peptides plotted against the percentage of cell adhesion.

Figure 9:
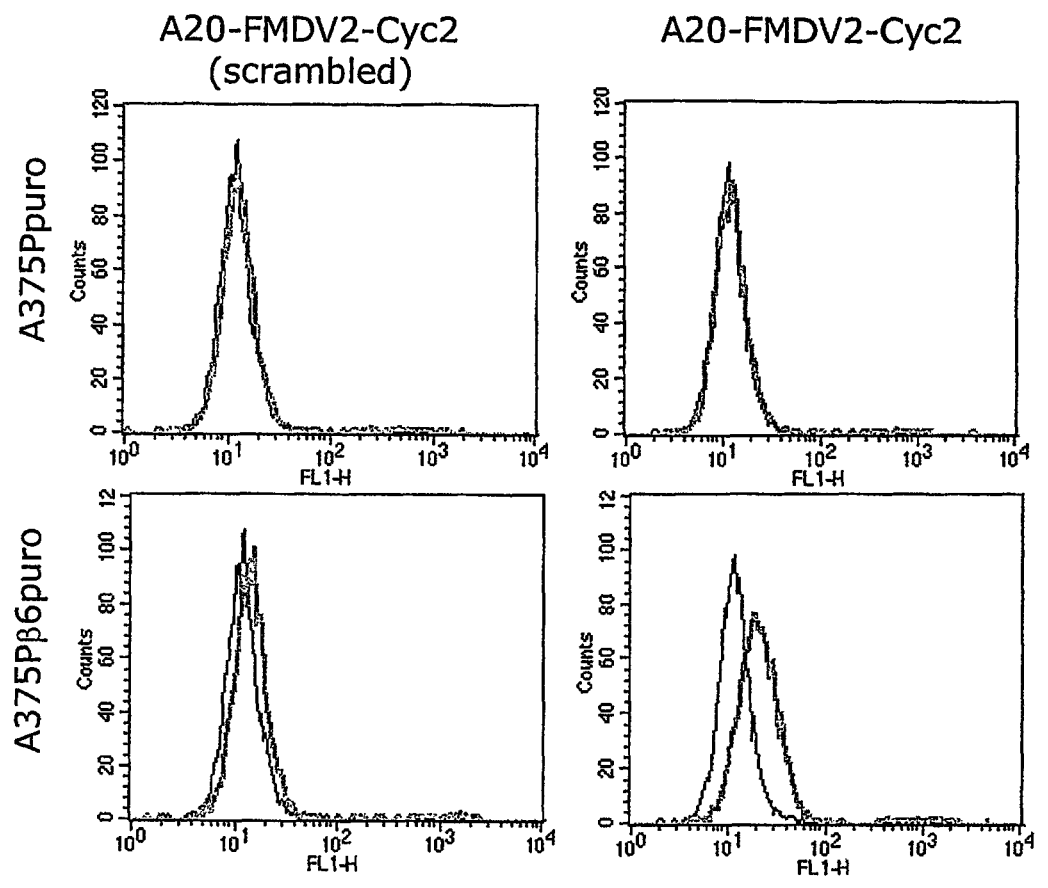

FIG. 9. Anti-αvβ6 cyclic peptides bind preferentially to αvβ6-expressing cells. Biotinylated A20FMDV2-Cyc2 or a cyclic scrambled version was added to A375Ppuro or A375Pb6puro cells. Bound peptide was detected with either streptavidin-FITC or mouse anti-biotin antibody followed by goat anti-mouse antibody conjugated to Alexa Fluor488 and samples analysed by flow cytometry. Peptide data are in light grey, background (streptavidin-FITC or mouse anti-biotin antibody followed by goat anti-mouse antibody conjugated to Alexa Fluor488 only) is shown in black. Note that the A20FMDV2-Cyc2 signal is higher on A375Pb6puro cells.

Figure 10:
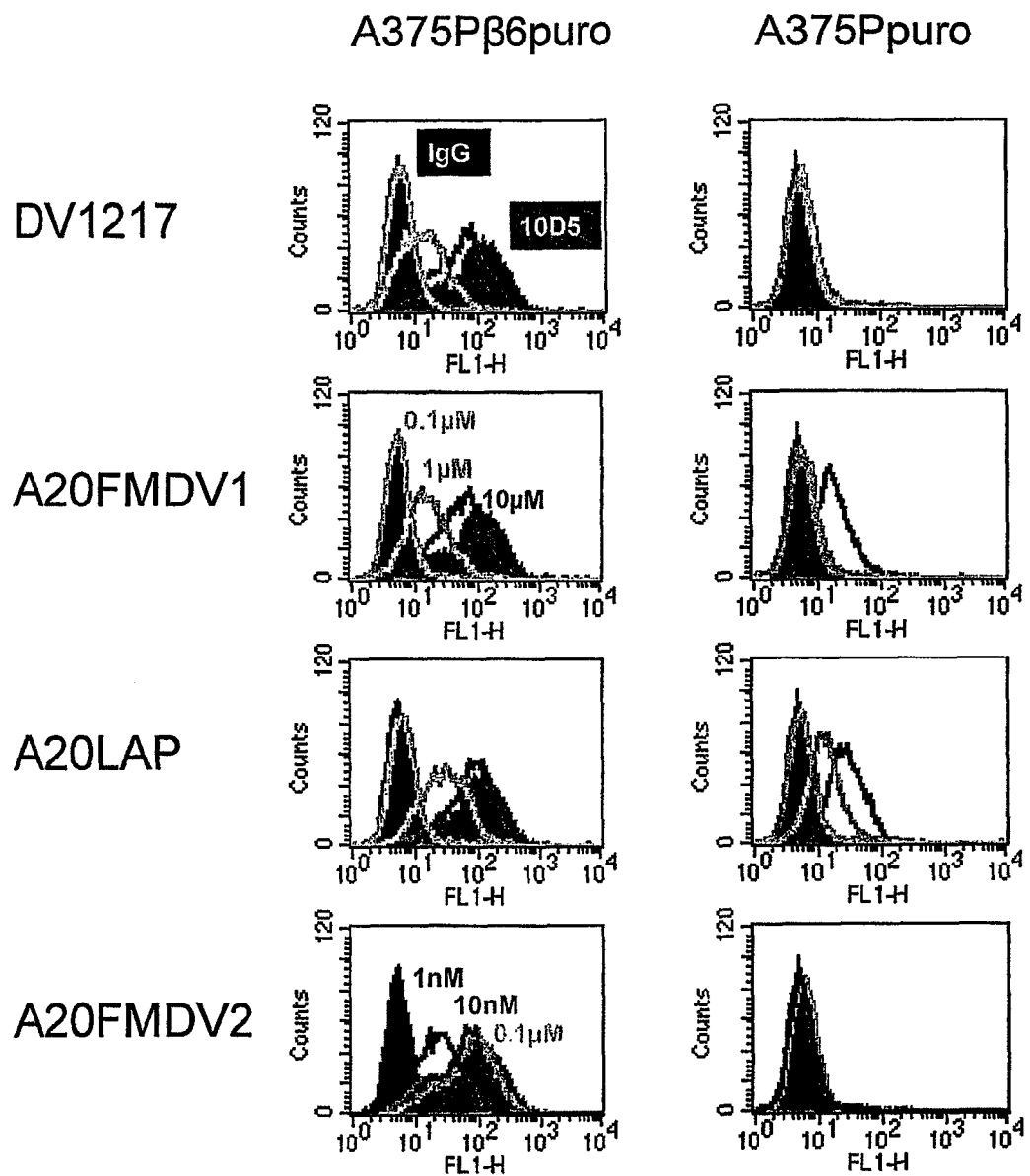

FIG. 10. Concentration-dependent binding of biotinylated peptides to A375Pβ6puro and A375Ppuro. Biotinylated peptides DV1217, A20FMDV1, A20LAP and A20FMDV2 were allowed to bind to A375Pβ6puro and A375Ppuro in the presence of cations (0.5 mM MgCl2, 1 mM CaCl2) and 0.1% sodium azide. Grey and black solids represent binding of control antibodies, 10D5 (anti-αvβ6, grey solids) and non-immune IgG (black solids). Red lines, 10 μM biotinylated peptide; orange lines, 1 μM biotinylated peptide; green lines, 0.1 μM biotinylated peptide; blue lines, 0.01 μM biotinylated peptide; purple lines, 0.001 μM biotinylated peptide. Data are representative of at least two independent experiments with similar results.

Table 1. NMR assignment list of observed 1H chemical shifts for A20FMDV, A20FMDV-2 and A20LAP peptides in PBS/30% (v/v) TFE at 10° C. All chemical shifts are referenced externally to a 100 μM solution of dimethylsilapetane sulphonic acid (DSS) in PBS/30% (v/v) TFE.

Table 2. List of NOE, hydrogen bond and torsion angle connectivities for A20FMDV, A20FMDV-2 and A20LAP peptides Table 3. Structural Statistics for 35 structure ensembles of A20FMDV, A20FMDV-2 and A20LAP peptides Table 4. Amino acid sequences of the peptides used in the experimental examples.

DETAILED DESCRIPTION

αvβ6 Peptide Ligands

The present invention involves the use of peptides ligands comprising the sequence motif RGDLX$^5$X$^6$L (SEQ ID NO: 1) or RGDLX$^5$X$^6$I (SEQ ID NO: 2), wherein LX$^5$X$^6$L or LX$^5$X$^6$I is contained within an alpha helical structure. Unless specified otherwise, amino acid positions herein are numbered from N to C-terminus of the peptide.

The term "alpha helical structure" is understood to be a sequential group of amino acids in a peptide that interact with a particular hydrogen bonding pattern and thus define a helical structure. For example, the hydrogen bonding pattern in a standard alpha helix is between the carbonyl oxygen of residue n and the amide hydrogen of residue n+4. For the 3$_{10}$-helix, this hydrogen bonding pattern is between residues n and n+3 and for a pi-helix it is between residues n and n+5. The number of residues per turn in each alpha-helix is 3.6, 3.0 and 4.4 for the standard alpha-helix, 3$_{10}$-helix and pi-helix respectively.

An alpha helix useful in the present invention may be an alpha helix mimetic as described in WO95/00534. Alpha helix mimetics are alpha helical structures which are able to stabilize the structure of a naturally occurring or synthetic peptide.

The peptides of the present invention may comprise standard helices, or 3$_{10}$ helices or pi helices or any combination thereof. For example, the helices of the present invention may comprise amino acids that form a "cap" structure, preferably two caps, an N terminal Cat and a C terminal cap which flank the helix.

In a preferred embodiment of the present invention, the peptide defined above comprises the sequence RGDLX$^5$X$^6$LX$^8$X$^9$X$^{10}$ (SEQ ID NO: 3). Preferably, the peptide comprises the sequence RGDLX$^5$X$^6$LX$^8$X$^9$X$^{10}$Z$_n$ (SEQ ID NO: 4), wherein Z is a helix promoting residue and n is any number between 1 and 20. Preferably, n is between 5 and 15, even more preferably n is between 8 and 12. Extension of the helix to include helical residues in the Z position are preferred embodiments as they further enhance the helix dipole that can also enhance binding to αvβ6.

The peptides of the present invention can also be functional variant of the peptides as defined above, including peptides that possess at least 70%, preferable 80%, even more preferable 90% sequence identity with the peptides above, it includes further peptides comprising unnatural or modified amino acids. Suitable unnatural amino acids include, for example, D-amino acids, ornithine, diaminobutyric acid ornithine, norleucine ornithine, pyriylalanine, thienylalanine, naphthylalanine, phenylglycine, alpha and alpha-disubstituted amino acids, N-alkyl amino acids, lactic acid, halide derivatives of natural amino acids, such as trifluorotyrosine, p-Cl-phenylalanine, p-Br-phenylalanine, p-I-phenylalanine, L-allyl-glycine, b-alanine, L-a-amino butyric acid, L-g-amino butyric acid, L-a-amino isobutyric acid, L-e-amino caproic acid, 7-amino heptanoic acid, L methionine sulfone, L-norleucine, L-norvaline, p-nitro-L-phenylalanine, L-hydroxyproline, L-thioproline, methyl derivatives of phenylalanine—such as 1-methyl-Phe, pentamethyl-Phe, L-Phe(4-amino), L-Tyr(methyl), L-Phe(4-isopropyl), L-Tic(1,2,3,4-tetrahydroisoquinoline-3-carboxyl acid), L-diaminopropionic acid and L-Phe(4-benzyl). The peptides may be further modified. For example, one or more amide bonds may be replaced by ester or alkyl backbone bonds. There may be N or C alkyl substituents, side chain modifications or constraints such as disulphide bridges, side chain amide or ester linkages.

The peptides of the present invention may include both modified peptides and synthetic peptide analogues. Peptides may be, for example, be modified to improve formulation and storage properties, or to protect labile peptide bonds by incorporating non-peptidic structures.

Peptides of the present invention may be prepared using methods known in the art. For example, peptides may be produced by chemical synthesis, e.g. solid phase techniques and automated peptide synthesisers, or by recombinant means (using nucleic acids such as those described herein). For example, peptides may be synthesised using solid phase strategies on an automated multiple peptide synthesizer (Abimed AMS 422) using 9-fluorenylmethyloxycarbonyl (Fmoc) chemistry. The peptides can then be purified by reversed phase-HPLC and lyophilized. The peptide may be prepared by cleavage of a longer peptide, e.g. the 5T4 peptide (GenBank Accession No. Z29083). Thus, the peptide may be a fragment of the 5T4 sequence. Peptides may be prepared by recombinant expression of the polynucleotides described herein.

Peptides are expressed in suitable host cells and isolated using methods known in the art.

Preferably, X$^5$-X$^6$ and X$^8$-X$^{10}$ are helix promoting residues. Preferably, the helix promoting residues are independently selected from the group consisting of Glu, Ala, Leu, Met, Gln, Lys, Arg, Val, Ile, Trp, Phe and Asp. The helix promoting residues could be an artificial amino acid or a modified amino acid.

The term "helix promoting residues" includes amino acids with a conformational preference greater than 1.0 for being found in the middle of an α-helix (from Creighton, 1993 and Pace C. N. and Scholtz J. M. (1998), Biophysical Journal, Vol. 75, pages 422-427). However, non-orthodox helix promoting combinations of amino acids are also within the scope of the invention if they enhance the specificity and/or affinity of binding to αvβ6.

By "terminal capping", we mean the stabilisation of the alpha helix dipole whereby the N-terminal end of the helix is capped by a negatively charged amino acid like glutamic acid. Likewise the C-terminal may be capped with a positively charged amino acid like lysine. Capping residues may adhere to capping rules as defined by Aurora and Rose (Protein Sci. 7(1):21-38; 1998), but non-orthodox capping motifs are also within the scope of the invention if they stabilize the peptide by structural interaction.

In a further embodiment, the peptides of the present invention may be cyclised. Methods are well known in the art for introducing cyclic structures into the peptides of the present invention to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclising methods include the formation of thioethers and carboxyl- and amino-terminal amides and esters. A number of synthetic techniques have been developed to generate synthetic circular peptides (Tam & Lu, Protein Sci., 7(7): 1583-1592, 1998; Romanovskis & Spatola, J. Pept. Res., 52(5): 356-374, 1998; Camarero & Muir, J. Amer. Chem. Soc., 121: 5597-5598, 1999; Valero et al., J. Pept. Res., 53(1): 56-67, 1999). Generally, the role of cyclising peptides is two fold: (a) to reduce hydrolysis in vivo and (b) to thermodynamically destabilise the unfolded state and promote secondary structure formation. There is some potential importance with hydrophobic packing of residues N-terminal to RGD along the opposite helix face so that the design of residues X5-X6 could also enhance specificity.

In a further embodiment of the present invention, the peptide may be represented by the following formula B$_n$RGDLXXLXXXZ$_m$ (SEQ ID NO: 5), where residue B is a residue which enhances the hydrophobic interactions with the helix defined from LXXL and also enhances the hammerhead RGD for binding, and wherein Z is a helix promoting residue and wherein n is a number between 1 and 35 and independently m is a number between 1 and 35. Preferably n selected so that B is sufficiently long to facilitate a hydrophobic/non-covalent interacting core. The exact nature of these residues depends on the general design of the region, in particular it is preferred to have a mixture of hydrophobic interactions (from residues such as Val, Ile, Leu) and/or electrostatic interactions (using Asp, Glu, Lys and Arg together with their counterpart ion-pair in the now defined X15-X16 positions (in between the two Leu residues in LXXL).

In a further embodiment, the peptide comprises or consists of a sequences selected from the group GFTTGRRGD-LATIHGMNRPF (SEQ ID NO: 6), YTASARGDLAHL-TTTHARHL (SEQ ID NO: 7) or NAVPNLRGDLQVLAQKVART (SEQ ID NO: 8).

In a further embodiment, the alpha helical structure of the peptide enables the hydrophobic side chains of the residues LXXL/I to protrude from one side of the helix.

In a further embodiment, the alpha helical structure has at least one turn.

In a further preferred embodiment, the peptide is between 7 to 45 amino acids long, preferably between 7 and 40, 35, 30, 25, 20, or 15 amino acids. For example, the peptide may be 7, 8, 9, 10, 11, 12, 13, 14, 22, 24, 26, 28, 32, 34, 36, 38, 42 or 44 amino acids in length. In any case, the peptide of the present invention should not exceed a length which would allow the formation of tertiary structure, typically a peptide should not exceed 45 amino acids if available as an isolated molecule. However, the peptide might exceed 45 amino acids if fused to a larger molecule such as an antibody or another protein or macromolecule which could prevent the formation of a tertiary structure within the peptide. Most preferably the peptide is 20 amino acids long.

In a further aspect, the peptides described herein may be linked to a readily detectable moiety. The term "readily detectable moiety" relates to a moiety which, when located at the target site following administration of the peptides of the invention into a patient, may be detected, typically non-invasively from outside the body and the site of the target located. Thus, the peptides of this embodiment of the invention are useful in imaging and diagnosis. Readily detectable moiety are entities that are detectable by imaging techniques such as Magnetic Resonance Imaging (MRI), Magnetic Resonance Spectroscopy (MRS), Single Photon Emission Computed Tomography (SPECT) and Positron Emission Tomography (PET) and optical imaging. Preferably, imaging moieties are stable, non-toxic entities that retain their properties under in vitro and in vivo conditions. Examples of such moieties include but are not limited to radioactive moieties, for example radioactive isotopes. Suitable radioactive atoms include technetium-99m or iodine-123 for scintigraphic studies. Other readily detectable moieties include, for example, spin labels for MRI such as iodine-123 again, iodine-131, indium-111, fluorine-18, carbon-13, nitrogen-15, oxygen-17, gadolinium, manganese or iron and optical moieties which include Cy5.5 and quantum dots.

In a further embodiment of the present invention a polypeptide is linked to a therapeutically active moiety, preferably the moiety is cytotoxic.

The term "therapeutically active moiety" encompasses a moiety having beneficial, prophylactic and/or therapeutic properties.

In one embodiment the therapeutically active moiety is a cytotoxic chemotherapeutic agent. Cytotoxic chemotherapeutic agents are well known in the art and include anticancer agents such as:

Alkylating agents including nitrogen mustards such as mechlorethamine (HN2), cyclophosphamide, ifosfamide, melphalan (L-sarcolysin) and chlorambucil; 10 ethylenimines and methylmelamines such as hexamethylmelamine, thiotepa; alkyl sulphonates such as busulfan; nitrosoureas such as carmustine (BCNU), lomustine (CCNLJ), semustine (methyl-CCN-U) and streptozoein (streptozotocin); and triazenes such as decarbazine (DTIC; dimethyltriazenoimidazolecarboxamide); Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycofonnycin). Natural Products including vinca alkaloids such as vinblastine (VLB) and vincristine; epipodophyllotoxins such as etoposide and teniposide; antibiotics such as dactinomycin (actinomycin D), daunorabicin (daunomycin; rubidomycin), doxorubicin, bleomycin, plicamycin (mithramycin) and mitomycin (mitomycin Q; enzymes such as L-asparaginase; and biological response modifiers such as interferon alphenomes. Miscellaneous agents including platinum coordination complexes such as cisplatin (cis-DDP) and carboplatin; anthracenedione such as mitoxantrone and antbracycline; substituted urea such as hydroxyurea; methyl hydrazine derivative such as procarbazine (N-methylhydrazine, MIH); and adrenocortical suppressant such as mitotane (o, p'-DDD) and aminoglutethimide; taxol and analogues/derivatives; and hormone agonists/antagonists such as flutamide and tamoxifen.

Methods of conjugating polypeptides to therapeutic agents are well known in the art.

In a further embodiment of the present invention a polypeptide is linked to a particle that contains the therapeutic agent. Particles in this instance include nanoparticles and lipid-based vesicles such as liposomes or other similar structures composed of lipids. Accordingly, the present invention provides the peptides as defined herein and a liposome carrier and nanoparticles comprising the peptides as defined herein.

Liposomes are a spherical vesicles comprising a phospholipid bilayer that may be used as agents to deliver materials such as drugs or genetic material. Liposomes can be composed of naturally-derived phospholipids with mixed lipid chains (egg phosphatidylethanolamine) or of pure components like DOPE (dioleolylphosphatidylethanolamine). The synthesis and use of liposomes is now well established in the art. Liposomes are generally created by sonication of phospholipids in a suitable medium such as water. Low shear rates create multilamellar liposomes having multi-layered structures. Continued high-shear sonication tends to form smaller unilamellar liposomes. Research has also been able to enable liposomes to avoid detection by the immune system, for examples by coating the lipsomes with polyethylene glycol (PEG). It is also possible to incorporate species in liposomes, such as the peptides of the invention to help to target them to a delivery site, e.g. in cells or in vivo.

The use of nanoparticles as delivery agents for materials associated with or bound to the nanoparticles is known in the art. Some types of nanoparticle comprises a core, often of metal and/or semiconductor atoms, to which ligands of one or more different types may be linked, including, for example, one or more of the peptides of the present invention, see for example WO02/32404, WO2005/10816 and WO2005/116226. Other types of nanoparticle may be formed from materials such as liposomes. In some instances, the nanoparticles may be derivatised or conjugated to other ligands may be present to provide the nanoparticles with different properties or functions. In some embodiments, the nanoparticles may be quantum dots, that is nanocrystals of semiconducting materials which have the striking chemical and physical properties that differ markedly from those of the bulk solid (see Gleiter, Adv. Mater. 1992, 4, 474-481). Now that their quantum size effects are understood, fundamental and applied research on these systems has become increasingly popular. An interesting application is the use of nanocrystals as luminescent labels for biological systems, see for example Brucher et al, Science 1998, 281, 2013-2016, Chan & Nie, Science, 1998, 281, 2016-2018, Mattousi et al, J. Am. Chem. Soc., 2000, 122, 12142-12150, and A. P. Alivisatos, Pure Appl. Chem. 2000, 72, 3-9. The quantum dots have several advantages over conventional fluorescent dyes: quantum dots emit light at a variety of precise wavelengths depending on their size and have long luminescent lifetimes.

In a further embodiment, the cytotoxic moiety is a cytotoxic peptide or polypeptide moiety by which we include any moiety which leads to cell death.

Cytotoxic peptide and polypeptide moieties are well known in the art and include, for example, ricin, abrin, *Pseudomonas exotoxin*, tissue factor and the like. The use of ricin as a cytotoxic agent is described in Burrows & Thorpe, P.N.A.S. USA 90: 8996-9000, 1993, incorporated herein by reference, and the use of tissue factor, which leads to localised blood clotting and infarction of a tumour, has been described by Ran et al, Cancer Res. 58: 4646-4653, 1998 and Huang et al, Science 275: 25 547-550, 1997. Tsai et al, Dis. Colon Rectum 38: 1067-1074, 1995 describes the abrin A chain conjugated to a monoclonal antibody and is incorporated herein by reference. Other ribosome inactivating proteins are described as cytotoxic agents in WO 96/06641. *Pseudomonas exotoxin* may also be used as the cytotoxic polypeptide moiety (see, for example, Aiello et al, P.N.A.S. USA 92: 10457-10461, 1995.

Certain cytokines, such as TNFα and IL-2, may also be useful as cytotoxic and/or therapeutic agents.

Certain radioactive atoms may also be cytotoxic if delivered in sufficient doses. Thus, the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the compound of the invention are such that a dose of more than 4000 cGy, and more preferably at least 6000, 8000 or 10000 cGy, is delivered to the target site and, preferably, to the cells at the target site and their organelles, particularly the nucleus.

The radioactive atom may be attached to the binding moiety in known ways. For example, EDTA or another chelating agent may be attached to the binding moiety and used to attach $^{111}$In or $^{90}$Y. Tyrosine residues may be labelled with $^{125}$ I or $^{131}$I.

In a further embodiment, the present invention provides a polypeptide is linked to viral coat protein other than FNDV to change the trophism of the virus for delivery of DNA encoding therapeutic genes.

Alternatively, any of these systems can be incorporated into a prodrug system. Such prodrug systems are well known in the art.

In other aspects, the present invention use nucleic acid encoding a peptide as defined herein.

The term "nucleic acid coding for" (a peptide) relates to an RNA or DNA sequence which encodes a peptide comprising the sequence motif RGDLX$^5$X$^6$L (SEQ ID NO: 1) or RGDLX$^5$X$^6$I (SEQ ID NO: 2), wherein LX$^5$X$^6$L or LX$^5$X$^6$I is contained within an alpha helical structure which can be used in accordance with the invention or a functional variant thereof or a precursor stage thereof, for example a propeptide or a prepropeptide. The peptide can be encoded by a full-length sequence or any part of the coding sequence as long as the peptide is a functional variant. The term "variants" denotes all the DNA sequences which are complementary to a DNA sequence (reference sequence), which encode peptides used in accordance with the invention, especially peptides as defined above or their functional variants and which exhibit at least approx. 70%, in particular at least approx. 80%, especially at least approx. 90%, sequence identity with the reference sequence. The term "variants" furthermore denotes all the DNA sequences which are complementary to the reference sequence and which hybridize with the reference sequence under stringent conditions and encode a peptide which exhibits essentially the same activity as does the peptide encoded by the reference sequence, and also their degenerate forms. It is known that small changes can be present in the sequence of the nucleic acids which can be used in accordance with the invention; for example, without the property of a functional variant being lost, these changes can be brought about by the degeneracy of the genetic code or by non translated sequences which are appended at the 5' end and/or the 3' end of the nucleic acid. This invention therefore also encompasses so-called "variants" of the previously described nucleic acids. The term "stringent hybridization conditions" is to be understood, in particular, as meaning those conditions in which a hybridization takes place, for example, at 60° C. in 2.5×SSC buffer, followed by several washing steps at 37° C. in a lower buffer concentration, and remains stable.

It is generally understood that the peptides and nucleic acids of the present invention can be of natural, recombinant or synthetic origin. Method of making, synthesising or modifying peptides are well known in the art. Suitable methods include chemical synthesis, polymerase chain reaction (PCR) amplification, cloning or direct cleavage from a longer polynucleotide. Polynucleotides of the invention have utility in production of the peptides of the invention, which may take place in vitro, in vivo or ex vivo. The polynucleotides may be used as therapeutic or immunisation agents in their own right or may be involved in recombinant peptide synthesis.

In a further aspect, the present invention provides a vector comprising a nucleic acid as defined herein.

The vector of the present invention is preferably an expression vector, preferably a eukaryotic expression vector which may be adapted for pharmaceutical applications.

A "vector" refers to a structure consisting of or including a nucleic acid molecule which is suitable for transferring genetic material into a cell. Typically a selected nucleic acid sequence is inserted into the nucleic acid molecule of the vector. Examples include plasmid and viral vectors. An "expression vector" is a vector constructed and adapted to allow expression of an inserted nucleic acid coding sequence in a cell. Thus, the vector includes nucleic acid sequences, which allow initiation of transcription in an appropriate location with respect to the coding sequence. Expression vectors can be adapted for expression in prokaryotic or eukaryotic cells, thus, a "eukaryotic expression vector" is constructed to allow expression of a coding sequence in a eukaryotic cell. Preferred examples of expression vectors of the present invention include adenovirus, AAV and lentiviruses.

In a further aspect, the present invention provides a pharmaceutical composition comprising peptide and/or nucleic acid and/or expression vector as defined above and a pharmaceutical acceptable carrier.

The term "pharmaceutically acceptable carrier" generally includes components that are compatible with the peptide, nucleic acid or vector and are not deleterious to the recipients thereof. Typically, the carriers will be water or saline which will be sterile and pyrogen free; however, other acceptable carriers may be used. Typically the pharmaceutical compositions or formulations of the invention are for parenteral administration, more particularly for intravenous administration.

In a further aspect, the present invention provides the use of a peptide and/or nucleic acid and/or expression vector according to the present invention for the preparation of a medicament for the treatment of a αvβ6 mediated disease or a disease where αvβ6 is overexpressed.

In a further aspect, the present invention provides a method of treating a αvβ6 mediated disease comprising administering a peptide and/or nucleic acid and/or expression vector and/or pharmaceutical composition as defined above to a patient. As mentioned herein, these conditions maybe in the general area of wound healing and inflammation.

Preferably, the disease is selected from chronic fibrosis, chronic obstructive pulmonary disease (COPD), lung emphysema, chronic wounding skin disease (e.g. epidermolysis bullosa) or cancer.

The medicament or pharmaceutical composition of the present invention as defined above may usefully be administered to a patient who is also administered other medicaments, as it will be known to those skilled in the art. For example, in the case of cancer, the medicament or pharmaceutical composition of the present invention may be administered to a patient before, after or during administration of the other anti-tumour agent(s), for example before, after or during chemotherapy. Treatment with the peptide after chemotherapy may be particularly useful in reducing or preventing recurrence of the tumour or metastasis. For example, the anti-tumour agent can be covalently linked directly or indirectly (via liposomes/nanoparticles) to a peptide of the invention.

In a further aspect, the present invention provides a method of imaging epithelial cells overexpressing αvβ6 in the body of an individual, the method comprising administering to the individual an effective amount of a peptide as defined above. The method is particularly useful for the imaging of chronic fibrosis, chronic obstructive pulmonary disease (COPD), lung emphysema, chronic wounding skin disease (e.g. epidermolysis bullosa) or epithelial tumour cells. For example, the method of imaging may include linking the targeting peptide to a fluorescent probe and incorporate into a mouth-wash, chewing gum, spray or other emolument such that the αvβ6 bound peptide-probe conjugate may be visualised by its fluorescent tag.

In a further aspect, the present invention provides a method for the diagnosis or prognosis in an individual of an αvβ6 mediated disease or a disease where αvβ6 is overexpressed, the method comprising administering to the individual an effective amount of a peptide as defined above and detecting the binding of the peptide to αvβ6.

In a further aspect, the present invention provides a method of delivering a therapeutic active moiety to a cell expressing αvβ6 or a tissue containing cells expressing αvβ6 in a patient, the method comprising administering a peptide linked to a therapeutic active moiety as defined above to the patent.

In a further aspect, the present invention provides a method of improving the binding specificity of an αvβ6 binding peptide by increasing or modifying the alpha helical content of the peptide. For example, the alpha helical content of the peptide may be increased by changing the residues within sequence $B_n$ RGDLXXLXXX $Z_m$ (SEQ ID NO: 5) into any other natural or synthetic amino-acid and measure the alpha helical content of the resultant peptides. Alternatively, peptide can be improved by using the Saturation Transfer Difference NMR to determine which residues in a peptide are most likely to be interacting directly with purified integrins (which may include α5β1, α8β1, αIIbβ3, αvββ1, αvβ3, αvβ5, αvβ6, αvβ8) and to subsequently insert residues as appropriate that possess particular side-chains, specific charge distribution or other modifications that will decrease binding to non-αvβ6 integrins or increase binding to αvβ6 integrins.

The term "improving the binding specificity" includes an increase in the affinity of a peptide to αvβ6 compared to its affinity to another integrin, for example αvβ3.

Examples

Cell Lines and Antibodies

Retroviral infection was utilised to generate αvβ6-positive and negative cell lines for this study. Mouse 3T3 fibroblasts and the human melanoma cell lines A375P and DX3 were infected with retroviruses (Thomas et al; J Invest Dermatol. 116(6):898-904, 2001) encoding human b6 and puromycin resistance gene to generate 3T3β6puro, A375Pβ6puro and DX3β6puro. Control cells expressed only puromycin (A375Ppuro and DX3puro-parental 3T3 cells served as controls for 3T3β6puro, sometimes called 3T3β6.19 or NIH3T3β6.19).

CHOβ6 cells, secreting recombinant-soluble αvβ6 lacking the cytoplasmic and trans-membrane domains of the integrin subunits. VB6 is a high αvβ6 expressing oral squamous carcinoma (Thomas et al, 2001) and V(+)B2 is a high αvβ1-expressing human melanoma (Marshall et al 1995). A variety of mouse monoclonal antibodies were used. Antibodies to αvβ3 (LM609), αvβ6(10D5) and a5 (P1D6) were purchased from Chemicon International, (Emecula Calif., USA). 63G9 (anti αvβ6) and 37E1 (anti-αvβ8). P2W7 (anti-αv; produced in-house), L230 (anti-αv; from ATCC), P1F6 (anti-αvβ5; a gift from Dr Dean Sheppard) and AIIB2 (anti-β1; purchased from Developmental hybridoma), were produced in-house from their respective hybridomas. Fibronectin (F2006; Sigma Aldrich) was biotinylated using a kit (Amersham International, UK) according to manufacturers instructions. All other reagents were purchased from Sigma-Aldrich unless stated otherwise.

Production of Recombinant Soluble αvβ6

CHOβ6 cells were grown to 80-90% confluency in RPMI supplemented with 10% fetal calf serum (FCS), washed once with low serum medium (LowSM; RPMI 0.5% v/v FCS) and incubated for 48 hours in LowSM. Cell debris was removed from conditioned medium by centrifugation at 982 g and 0.1% (w/v) sodium azide was added as a preservative.

Conditioned medium was concentrated (up to 300-fold) and simultaneously diafiltrated against PBS using Centricon Plus-80 centrifugal filter devices with a cut-off of 100 kDa (Millipore). The concentrate was added to an immunoaffinity column that was generated by conjugating the mouse monoclonal anti-αv antibody L230 (in Coupling Buffer 0.1M Sodium Phosphate buffer, pH 7.0) to a 7 ml, gravity-flow agarose bead column using the Carbolink kit (Perbio Science UK Ltd) according to the manufacturers instructions. Recombinant soluble αvβ6 (rsαvβ6) was eluted with 100 mM glycine pH 2.5-3.0 and neutralised immediately by addition of 300 µl 1M Tris pH 7.5 to each 2 ml fraction. Peak fractions were selected according to their absorbance at 280 nm and dialysed against PBS using Amicon Ultra-15 centrifugal filter devices with a nominal molecular weight cut-off (NMWCO) of 50 kDa (Millipore). Purity of the eluted protein was determined by SDS-PAGE and the concentration determined by BioRad DC Protein Concentration Assay, using BSA standards. Functional integrity of the rsαvβ6 was confirmed by showing the integrin bound to fibronectin and latency-associated peptide(LAP) (αvβ6 ligands) immobilised to 96-well plates.

Cell Adhesion Assays

Adhesion of [$^{51}$Cr]-labelled cells to 96-well flexible plates coated with ECM ligands has been described previously (Thomas et al, 2001). Briefly, plates were coated with LAP (0.25 µg/ml for NIH 3T3B6.19, 0.5 µg/ml for VB6) or vitronectin (10 µg/ml; BD Biosciences, Oxford, UK). Cells were allowed to adhere for 40 minutes (VB6, NIH 3T3 β6.19) or 60 minutes (V+B2) before the plate was washed twice in PBS supplemented with cations (0.5 mM Mg$^{2+}$, 1 mM Ca$^{2+}$). Plates were cut with scissors and the radioactivity of each well quantified in a Wizard 1470 Automatic Gamma Counter (Perkin-Elmer, Boston, Mass., USA). The percentage adhesion was calculated by comparing the residual radioactivity associated with each well with the radioactivity of the initial input of cells as follows:

$$\text{Adhesion (\%)} = \frac{\text{Residual radioactivity (cpm) of well}}{\text{Radioactivity (cpm) of input}} \times 100$$

All samples were tested in quadruplicate wells in at least three separate assays.

Competitive Sandwich ELISA 96-well plates (Immulon IB, Thermo LifeSciences) were coated with 10 µg/ml P2W7 in PBS at 4° C. overnight then blocked by incubation with 2% (w/v) casein in PBS before washing with PBS. All subsequent washes used Wash Buffer (20 mM Tris, 150 mM NaCl, 1 mM MnCl$_2$), and all subsequent incubations took place in Conjugate Buffer (1% Casein, 20 mM Tris, 150 mM NaCl, 1 mM MnCl$_2$). Wells were incubated with rsαvβ6 for one hour, washed, and exposed to a premixed solution of peptide and 2 µg/ml biotinylated fibronectin. Bound biotinylated fibronectin was detected with ExtrAvidin HRP (SIGMA) at a dilution of 1:1000, and developed using the TMB+ system (DAKO). Assays were quantified by reading absorbance at A450 nm on a Tecan GENios plate-reader. All data was in the linear range, confirmed by a standard curve of biotinylated fibronectin on each plate.

Flow Cytometry

Expression of integrins by cell lines was assessed by flow cytometry as described previously (Marshall et al., 1995). Briefly, cell suspensions were incubated with anti-integrin antibodies at 10 µg/ml or biotinylated peptides at various concentrations. After 45' at 4° C., cells were washed and bound antibody/peptide was detected by 30' incubation with mouse anti-biotin (1:100, Stratech, UK) followed by an additional incubation for 30 minutes with Alexafluor 488 conjugated anti-mouse IgG (1:500 final dilution; Molecular Probes) or Streptavidin-FITC ((1:200 final concentration) respectively. Cells were analysed on a FACScan (Becton-Dickinson) fitted with CellQuest software capturing 10,000 events per sample.

Peptide Synthesis

Peptides were synthesised using standard solid-phase peptide synthesis by the Cancer Research UK Peptide Synthesis laboratory. Briefly, protected amino acids and pre-loaded Wang resins were obtained from Calbiochem-Novabiochem (Nottingham, UK). Solvents and HBTU [2-(1H-benzotriazol-1-yl)-1,1,3,3-tetramethyluronium hexafluorophosphate] were obtained from Applied Biosystems (Warrington, UK). The peptides were synthesised on a Model 431A updated and 433A Applied Biosystems Solid Phase Synthesiser on preloaded Wang resin using basic feedback monitoring cycles and HBTU as a coupling reagent. 9-fluorenylmethyloxycarbonyl was used for temporary a-amino group protection and removed using piperidine. Side-chain protecting groups were tert-butyloxycarbonyl for Lys; trityl for His, Asn and Gln; 2,2,5,7,8-pentamethylchroman-6-sulphonyl for Arg; tert-butylester for Glu and Asp and tert-butyl ether for Thr, Ser and Tyr.

Cleavage from the resin and deprotection of the peptides was achieved by treating the peptidyl-resin with 10 mls of a mixture containing 9.25 mls trifluoroacetic acid, 0.25 mls ethanedithiol, 0.25 mls triisopropylsilane and 0.25 mls water at 20° C. (room temp) for 4 hours. The peptide was precipitated using ice-cold diethylether and then filtered on a fine sintered glass filter funnel under light vacuum. The peptide precipitate was dissolved in 10% acetic acid/water solution and freeze dried.

The crude peptides were purified by reverse phase HPLC on an Aquapore ODS 20 micron 250×10 mm column and the authenticity of the purified peptide was then confirmed by MALDI-TOF (matrix assisted laser desorption ionization time of flight) mass spectroscopy on a Finnigan MAT LCQ ion-trap mass spectrometer. Some peptides were biotinylated in situ on resin support using standard procedures.

NMR Sample Preparation

All NMR samples were prepared to a final volume of 300 µL for use in a Shigemi BMS005V NMR tube by dissolving purified, freeze-dried peptide in 2 mM phosphate buffered saline (PBS) at pH 6.4 with a phosphate concentration of 25 mM and saline concentration of 100 mM. For structural studies, trifluoroethanol-d3 (TFE) was added as a helix stabilizer to provide a final concentration of 30% (v/v). Saturation Transfer Difference NMR (STDNMR) samples were prepared similarly with additional components: 28 µM integrin αvβ6, 0.5 mM Mg$^{2+}$ (added as MgCl$_2$) and 1.0 mM Ca$^{2+}$ (added as CaCl$_2$). STDNMR samples contained no TFE.

NMR Spectroscopy

All experiments were recorded on a Varian Unity INOVA 600 MHz NMR spectrometer with a z-shielded gradient triple resonance probe using standard procedures. Structural experiments, run at 10° C. for each peptide sample included two-dimensional (2D) nuclear Overhauser effect spectroscopy (NOESY), total correlation spectroscopy (TOCSY) and rotating frame Overhauser effect spectroscopy (ROESY) experiments that were recorded with mixing times of 250, 70.0 and 100 ms respectively. These experiments were collected with 512 and 1024 complex points with acquisition times of 64 and 128 ms in the indirectly and directly acquired 1H dimensions respectively. In addition, a two-dimensional double-quantum-filtered correlated spectroscopy (DQFCOSY) experiment was collected for each peptide at 10° C., with 1024 and 2048 complex points with acquisition times of 128 and 256 ms in the indirectly and directly acquired 1H dimensions respectively. Slow exchanging amide protons were detected from the fingerprint region of a 50 ms mixing time NOESY experiment that was collected with 128 and 1024 complex points with acquisition times of 16 and 128 ms in the indirectly and directly acquired 1H dimensions respectively. Data processing and analysis were carried out on Sun Blade 100, Silicon Graphic Octane2 and Transtec X2100 Linux workstations using NMRPipe (Delaglio et al, 1995) to process and NMRView (Johnson and Blevins, 1994) to view calculated structures. Saturation Transfer Difference NMR (STD NMR) experiments were run using standard saturation transfer experiment as described by Mayer and Meyer (1999, 2001), but incorporating a Hahn-echo filter as described by Yan et al, 2003. STD difference data were obtained at 25° C. with a spectral width of 6000 Hz, using a Hahn-Echo filter length of 30 ms and a total number of data points and transients of 8192 and 16384 respectively. On resonance irradiation was set to −2.5 ppm and off resonance irradiation was set to −70.0 ppm. Irradiation was applied using a train of 9.4 ms Gaussian pulses, each with 100 Hz bandwidth with each pulse separated by a 1.7 ms delay. The total pulse train was applied for 2.0 s. In order to enable assignment of STD NMR transfer data, peptide assignments were made from (2D) nuclear Overhauser effect spectroscopy (NOESY), total correlation spectroscopy (TOCSY) and rotating frame Overhauser effect spectroscopy (ROESY) experiments obtained at 25° C. Resonance volume integrals were obtained using VNMR software operating on a SUN UNIX workstation and the data analysed in accordance with the methods outlined by Mayer and Meyer (2001) to obtain the STD amplification factor using a ligand excess of 71.4. An individual amplification factor was obtained for each amino acid residue from a sum of amplification factors from each 1H resonance for each residue. The residue amplification factor was converted to residue percentage STD amplification factors to enable a comparison with the highest residue factor (that was given 100%).

Circular Dichroism

CD spectra were recorded on a Jasco J-600 spectropolarimeter at room temperature using 0.4 mM concentrations of peptide in buffers identical to those used in the NMR investigations and containing TFE between 0-50% (v/v). Each solution was loaded onto 5 mm path length quartz cuvettes and each spectra obtained from an average of 4 scans at a range between 190 and 260 nm, recorded at the speed of 20 nm/min, with a bandwidth of 1 nm, a response of 2s, and a resolution of 0.2 nm. The spectra are shown with no baseline correction. The OD values obtained by the spectropolarimeter were converted into ellipticity and adjusted to the relative peptide concentrations by the J-700 windows standard analysis (v.1.50.01) software. The ellipticity values at 3 wavelengths: 222, 208 and 192 nm were then converted into the mean ellipticity (meanq) obtained for each peptide at TFE concentrations between 0-50% (v/v) using the approach as described in Forood et al. 1993.

Structural Calculations and Analysis

All structural calculations were obtained using the Crystalography and NMR System (CNS) version 1.1 running on Silicon Graphics Octane2 and Transtec X2100 Linux workstations (Brunger et al, 1998). All NOE and ROE contacts were classified into one wide classification between 2.5-5.0 Å with final structures calculated from extended coordinates using the standard CNS NMR anneal protocol with sum averaging for dynamic annealing with constraints from both extended and folded precursors. A final structural ensemble of 40 structures for each peptide was produced with all structures used to produce statistical energy and root mean square (r.m.s.) deviation structural information. Backbone and heavy atom r.m.s. deviation values were obtained using MOLMOL version 2k.2 (Koradi et al, 1996) on a PC running Microsoft Windows 2000. The structural integrity of each ensemble was evaluated using PROCHECK-NMR (Laskowski et al, 1996) run on a Transtec X2100 Linux workstation. Energy comparisons between structure ensembles created in CNS were made using GROMOS96 43B1 parameter set (van Gunsteren, 1994) within DEEP-VIEW version 3.7 (Guex and Peitsch, 1997).

Results

Peptides Derived from αvβ6 Ligands Confirms Requirement for DLXXL

The integrin αvβ6 binds to its ligands, in part, through recognition of the peptide motif RGD (Arg-Gly-Asp). Ligands of the integrin αvβ6 include the TGFβ latency associated peptide (LAP), which we have found to be a highly specific αvβ6 adhesive ligand, fibronectin and certain viruses including foot-and-mouth-disease virus (FMDV). We therefore chose to examine overlapping 7-12 mer linear peptides from known αvβ6 ligands, that included the necessary RGD motif, from LAP and two serotypes of FMDV (DD1-DD19). In initial studies, the peptides were tested at a concentration of 500 μM for their ability to inhibit αvβ6-dependent adhesion to LAP of the tumour cells 3T3β6.19 and VB6. It was shown that the most potent peptides had the sequence DLXXL (or the similar DLXXI), a sequence whose importance had been discovered previously (Kraft et al, J Biol Chem. January 22; 274(4):1979-85. 1999).

Second Generation αvβ6-Targeting Peptides: Ligand-Based, 20Mer, RGDLXXL/I SEQ ID NO: 1/SEQ ID NO: 2) Peptides There was also a suggestion that longer peptides or at least those with more residues C-terminal to the RGD motif, were more potent inhibitors of αvβ6-dependent adhesion, compared to peptides with additional N-terminal sequence. To examine this possibility, we generated 20 mer peptides with extended C-terminal regions derived from LAP β1 (A20LAP) and the foot and mouth disease virus serotypes C-S8c1 (A20 FMDV1—Mateu et al., 1996) and O1BFS (A20 FMDV2—Logan et al., 1993) and repeated the experiments.

```
A20 LAP
                                         (SEQ ID NO: 6)
GFTTGRRGDLATIHGMNRPF

A20 FMDV-1
                                         (SEQ ID NO: 7)
YTASARGDLAHLTTTHARHL

A20 FMDV-2
                                         (SEQ ID NO: 8)
NAVPNLRGDLQVLAQKVART
```

Figure 2:
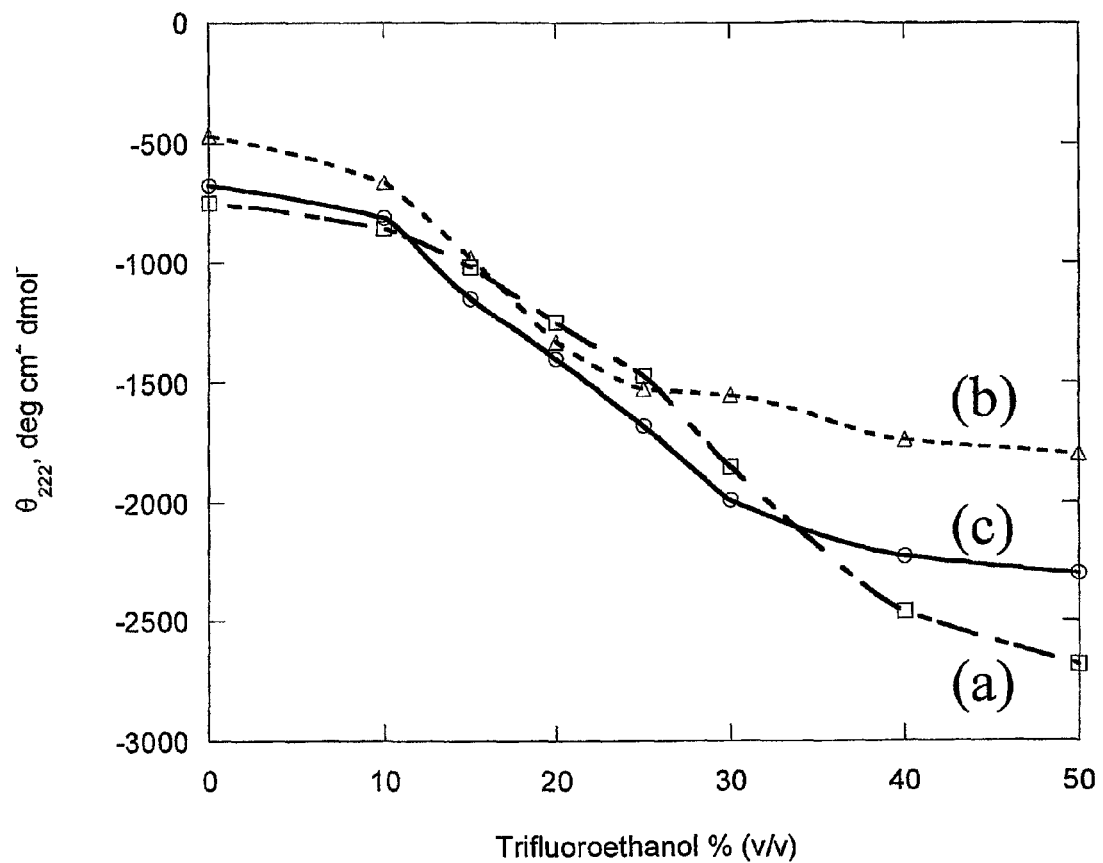
FIG. 2. Mean molecular elipticity of (a) A20FMDV1, (b) A20FMDV2 and (c) A20LAP peptides in PBS with TFE concentrations between 0-50% (v/v).

FIG. 2 confirms that A20 LAP, A20 FMDV and A20 FMDV2 were far more potent at inhibiting αvβ6-dependent binding of 3T3β6.19 (FIG. 2A) and VB6 (FIG. 2B) to LAP. Thus whereas the IC50 of DD1 inhibition of 3T3β6.19, the best short LAP peptide, is 216 μM (data not shown), the IC50 for A20 LAP is 13.8 μM. Similarly, the IC50 for DD19, the short FMDV2 peptide, is 190 μM compared with 1.2 μM for A20FMDV2.

20Mer RGDLXXL/I (SEQ ID NO: 1/SEQ ID NO: 2) Peptides are More Potent Inhibitors of αvβ6-Dependent Cell Adhesion than Shorter RGDLXXL/I (SEQ ID NO: 1/SEQ ID NO: 2) Peptides In order to test the hypothesis that an extended C-terminal sequence increases the efficacy of anti-αvβ6 peptides, the αvβ6-specific activity of A20LAP was compared with shorter versions of the same peptide, DD1, 2 and 3. A20LAP was significantly better at inhibiting αvβ6-dependent cell adhesion of 3T3β6.19 to LAP-coated plates. Thus, the number of amino acids C-terminal to RGD for A20LAP, DD1 and DD3 is 11, 5 and 4, respectively. This replicates the potency order of the peptides; thus in the presence of 20 μM A20-LAP, DD1 and DD3, adhesion of 3T3β6.19 to LAP was just 32±7%, 57±4% and 79±22% of control cell adhesion respectively. In addition, the experiments were repeated using another cell line, VB6. VB6 is a human oral squamous cell carcinoma that expresses high levels of αvβ6 (Thomas et al, 2001b). It is thus a more appropriate model since entirely human αvβ6 is expressed in its natural, epithelial environment. Similarly to 3T3β6.19, adhesion of VB6 to LAP is abrogated by the αvβ6-blocking antibody 63G9 and is, therefore, considered entirely αvβ6-dependent. Whilst difficult to quantitate due to intra-assay variation, the same pattern as was seen with 3T3β6.19 is broadly observable in assays using VB6. Thus at 100 μM DD1, DD2 and DD3 have little effect on VB6 adhesion to LAP, while the longer peptide A20LAP completely blocks cell adhesion at this concentration.

Similarly, A20FMDV2 is a markedly better inhibitor of VB6 adhesion to LAP than DD19, a shorter peptide based on the same amino acid sequence. The effect here is more dramatic: cell adhesion in the presence of 20 μM DD19 is the same as adhesion in the absence of peptide, however adhesion is reduced to background levels in the presence of 20 μM A20FMDV2.

Competitive Sandwich ELISA

To see if this pattern was repeatable in an isolated protein assay, competitive sandwich ELISAs were performed. Briefly, 96-well plates were coated with the anti-αv antibody P2W7 by incubating overnight at 4° C. Remaining non-specific binding sites were blocked by incubation with a solution of 2% (w/v) casein in PBS. Wells were then incubated with rsαvβ6 before washing and exposure to a pre-mixed solution of biotinylated fibronectin and peptide. Bound biotinylated fibronectin was detected with peroxidase-conjugated ExtrAvidin. Nine-point dose response curves were generated using seven concentrations of peptide and positive and negative controls, and an IC50 concentration determined using a sigmoidal curve-fit model with GraphPad Prism software.

Interestingly, the pattern seen in competitive sandwich ELISA is slightly different to that seen in cell adhesion assays. Although the short LAP-based peptides DD2 and DD3 have a significantly lower IC50 than the longer peptide A20LAP, the short peptide DD1 has a very similar IC50 to A20LAP.

TABLE 5

| Peptide | Sequence (SEQ ID NO) | Mean IC50 (nM) | Standard Deviation (nM) |
| --- | --- | --- | --- |
| DD1 | RRGDLATIH (9) | 9.2 | 0.7 |
| DD2 | FTTGRRGDLATI (10) | 30.9 | 3.3 |
| DD3 | TGRRGDLATI (11) | 22.6 | 4.0 |
| A20LAP | GFTTGRRGDLATIHGMNRPF (6) | 6.7 | 0.9 |
| DD19 | VPNLRGDLQVLA (12) | 85.0 | 31.1 |
| A20FMDV2 | NAVPNLRGDLQVLAQKVART (8) | 15.6 | 5.3 |

Analysis of 20Mer RGDLXXL/I (SEQ ID NO: 1/SEQ ID NO: 2) Peptides by Cell Adhesion Assay The three 20 mer peptides A20LAP, A20FMDV1 and A20FMDV2 were assessed for inhibition of αvβ6-dependent cell adhesion. Multiple concentrations of peptide were used in order to generate inhibition curves, from which IC50 values were calculated using Prism Software as shown in the table below. In both 3T3β6.19 and VB6 assays, A20FMDV2 was the most potent inhibitor of αvβ6-dependent cell adhesion, followed by A20LAP. A20FMDV1 was the least potent inhibitor in both assays. Therefore, predicted helicity correlates with peptide potency in inhibition of αvβ6-dependent cell adhesion assays. Interestingly, the IC50s for all peptides were approximately 1,000-fold higher in cell adhesion assays than in competitive ELISAs; this effect has been reported previously for anti-αvβ3 peptides (Goodman et al, 2002).

TABLE 6

| Peptide | Sequence | 3T3β6.19 | VB6 |
| --- | --- | --- | --- |
| A20FMDV1 | YTASARGDLAHLTTTHARHL (SEQ ID NO: 7) | 86.5 ± 49.9 μM | 38.2 ± 31.1 μM |
| A20LAP | GFTTGRRGDLATIHGMNRPF (SEQ ID NO: 6) | 13.8 ± 3.3 μM | 28.7 ± 11 μM |

TABLE 6-continued

| Peptide | Sequence | 3T3β6.19 | VB6 |
|---------|----------|----------|-----|
| A20FMDV2 | NAVPNLRGDLQVLAQKVART (SEQ ID NO: 8) | 1.2 ± 0.2 µM | 1.54 ± 0.4 µM |

Binding Hierarchy of 20Mer Peptide Antagonists

To compare the binding abilities of each peptide for αvβ6, rsαvβ6 was immobilised on 96-well plates. Various concentrations of biotinylated-A20 FMDV1, -A20 LAP or -A20 FMDV2 were added to the plates for 45' in the presence of 1 mM $Ca^{2+}$ and 0.5 mM $Mg^{2+}$ ions. Bound peptide was detected with streptavidin-HRP. In addition, biotinylated, scrambled versions of each peptide were also tested. FIG. 3 shows that the ability to bind αvβ6 followed the order A20 FMDV2, A20 LAP and A20 FMDV1. Thus at all concentrations A20 FMDV2 bound more strongly to the immobilised rsαvβ6. At 10 nM concentrations each peptide still exhibited near maximal binding in contrast to scrambled controls which showed no binding. Even at 1 nM A20 FMDV2 showed 50% maximal binding. Interestingly, scrambled A20 LAP did show binding at 10 μM and 1 μM in contrast to scrambled FMDV peptides which showed little binding at any concentration tested.

AGADIR Predicts Helical Propensity of 20 mer αvβ6 Antagonists

For both LAP- and FMDV-based peptides, longer peptides inhibited αvβ6 with a greater degree of potency than shorter peptides, even when all the peptides concerned contained the crucial RGDLXXL/I (SEQ ID NO: 1/SEQ ID NO: 2) motif. However, aside from this motif, there are no obvious similarities between the sequences of A20LAP and A20FMDV2; therefore it was considered unlikely that the motif had simply been extended in the longer peptides. Another possible explanation was that the increased length causes a change in the affinity of the peptide for αvβ6 by changing the presentation of the RGDLXXL/I (SEQ ID NO: 1/SEQ ID NO: 2) motif. The presence of secondary structure, which could potentially stabilise active conformations of RGDLXXL/I (SEQ ID NO: 1/SEQ ID NO: 2), was therefore considered.

Intuitively, long linear peptides are more likely to be able to assume many more shapes in three-dimensional (3D) space than shorter peptides and few of these long shapes are likely to be optimal ligands for a receptor. Since in our experiments the longer peptides were more potent inhibitors of αvβ6 than shorter peptides this suggested that there may be secondary structure minimising the number of possible 3D conformations. In solution, the VP1 coat protein is unstructured (Logan et al 1993). However, Logan and colleagues characterised the crystal structure of the immunogenic G-H loop of the VP1 domain of FMDV. They reported that the loop appeared to have a helical structure in the crystal. Thus we considered that our 20 mer peptides may also have helical structures which thermodynamically would stabilize the structure. We inserted the amino-acid sequences into AGADIR (Munoz and Serrano, 1994, 1995) software that predicts helical propensity within peptides. The software assigns probability values that individual residues in a peptide sequence are part of a helical structure. This software is widely acknowledged as a reasonably accurate method of predicting helicity. FIG. 3 shows that all three 20 mer peptides are predicted to have a helical propensity in the DLXXL/I region in the order A20 FMDV2>A20 LAP>A20 FMDV1 but that A20 FMDV2 has a much greater predicted helical propensity than either A20 LAP or A20 FMDV1 and it extends beyond DLXXL/I. Thus, the predicted helical propensity of the 20 mer peptides correlates with their potency as αvβ6 antagonists. To test this hypothesis the three 20 mer peptides were studied in more detail, both biochemically and structurally.

Far-UV CD Analysis

Circular dichroism is an optical technique based on the changes in polarisation that occur when UV light passes through a chiral environment. Differential absorption of left- and right-polarised light causes circularly polarised light to become elliptically polarised. The differing chiral environments of the different forms of secondary structure (beta-sheets, turns and helices; also the unstructured 'random coil' state) cause each to have their own characteristic far-UV CD spectra; therefore CD can be used to study the amount of each type of secondary structure in a particular protein or peptide.

To confirm whether our 20 mer peptides formed helical structures we determined the far-ultraviolet circular dichroism (Far-UV CD) spectra for each peptide in increasing concentrations of the helix stabilizer, TFE (FIG. 1). To enable cross-comparison between samples, the mean residue ellipicity (θ-[q]222) for each peptide in TFE proportions between 0-50% (v/v) in PBS are shown in FIG. 1. FIGS. 2 (*a-c*) each illustrates an isodichroic point at 202 nm that indicates that a two-state equilibrium exists between the unfolded and the helical peptide state for each peptide (Khandelwal et al, 1999). The mean molecular ellipticity identifies that both A20FMDV2 and A20LAP undergoes transition to helix between 10-25% TFE whereas A20FMDV1 undergoes transition over a much wider concentration range (10-40% v/v in PBS) of TFE. Thus, CD data show that if a stabilizing influence is present all three 20 mer peptides form helices in their structure but that there is an increased propensity for A20 FMDV2 and A20 LAP to form helices compared with A20FMDV1. Empirically-determined helical propensity therefore correlates with anti-αvβ6 potency.

NMR Analysis of αvβ6 20 mer-Peptide Antagonists

Spin systems were identified by analysis of two-dimensional DQF-COSY and TOCSY NMR spectra together with resonance assignments and all the observed $^1$H chemical shifts are listed in Table 3. Assignments for the majority of nuclei in all $^1$H spin systems were possible for A20FMDV1, A20FMDV2 and A20LAP peptides except for Thr2 of A20FMDV and Gly1 of A20LAP.

Through-space assignments were achieved using two-dimensional NOESY and ROESY spectra of each peptide in 30% TFE (v/v). Amides in slow exchange and deemed capable of being hydrogen bond donors were originally identified from a NOESY experiment obtained after re-suspension of each peptide in D20 and confirmed by visual inspection of intermediate structures from CNS calculations. Additional f restraints were obtained from application of the Karplus relationship to 3JHNHa that were obtained from high-resolution DQF-COSY spectra. 3JHNHa values less than 5 Hz were used to constraint f for that residue to −60°±30°. A cut off value of 5 Hz was used to allow for the fact that 3JHNHa values obtained by DQF-COSY are always larger than those obtained by more accurate heteronuclear NMR methods (Cavanagh et al., 1996).

The contact distribution of NOE and ROE was found to be greater for residues in the C-termini following from RGD in each of the peptides studied. A summary of the number of contact types and additional restraints are shown in Table 4 with the distribution of restraints across each peptide shown in FIGS. 3(a), (b) and (c). Contact types observed in FIG. 3(a) support standard helix conformations directly C-terminal to the RGD motif with contacts observed between Ha:i and HN:i+3 as well as Ha:i and Hb:i+3. Additionally, slow HN exchange and 3JHNHa values less that 5 Hz were observed in some residues as shown in FIG. 6.

Figure 4:
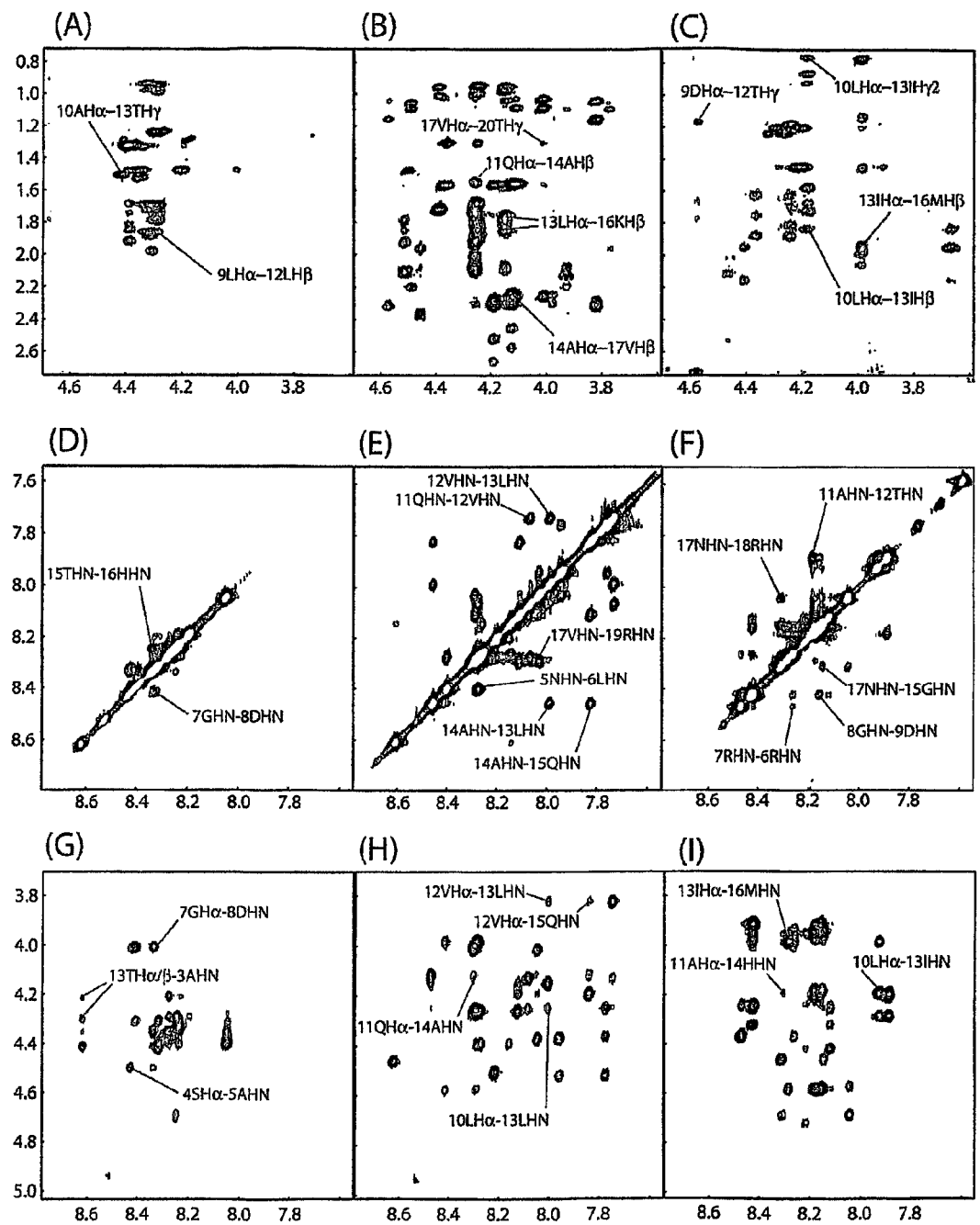
FIG. 4. Sections of 2D NOESY NMR Spectra for A20FMDV1: (a), (d) and (e); A20FMDV2: (b), (e) and (h) and A20LAP: (c), (f) and (i). Spectra (a-c) cover the Ha-Hb region, (d-f) the NH-NH region and (g-I) the NH-aH region.

FIG. 4 highlights the main helical contact regions of 2D NOESY spectra for all three peptides and demonstrates that the number of contacts and resonance dispersion is greatest with A20FMDV2 and least with A20FMDV1. Contacts that support helical character appear most sporadic in A20FMDV1 and best defined in A20FMDV2 with the A20LAP contact distribution falling between these two extremes.

Structure Calculations and Analysis

NMR was used to determine the solution structures of the three 20 mer peptides, and thus to confirm the CD and the in silico (AGADIR) data. NMR data generates a series of constraints, for example in the form of Nuclear Overhauser Effects (NOEs). NOEs are observed when two atoms are close enough in space for NMR spectroscopic relaxation to occur between them. If the two atoms are identified as being non-adjacent in the primary sequence, each NOE provides evidence to support the presence of secondary structure that maintains these regions in close proximity. Furthermore, the NOEs provide distance constraints that can be tabulated and used in tandem to produce a model of the structure. Constraints such as these limit the number of peptide conformations that are physically possible; a computer algorithm is then used to generate a number of conformations (known as ensembles) that fit the constraints.

All structural data was determined using CNS as described in the experimental procedures. No calculated structure gave violations greater than 0.2 Å or bond angle violations greater than 5° when all 40 structures were used to compute the ensemble average structural set. Structural energy statistics and backbone r.m.s. deviations for all three peptides are all shown in Table 3 and all ensembles and ensemble average structures are shown in FIG. 5. Backbone r.m.s. deviations are quoted over residues LXX[L/I]XX for each peptide to enable comparative analysis of each peptide. PROCHECK-NMR analysis for each of the 40-structure ensembles identified that 94.3, 94.8 and 93.6% of all residues fell in the allowed regions of the Ramachandaran plot for A20FMDV1, A20FMDV2 and A20LAP respectively. Residues that fell outside the allowed regions were from the first four amino acids in each ensemble and their deviations were consistent with data obtained from structure calculations for regions where little or no restraint data is given. Helix limits shown in FIG. 3 and FIG. 5 were identified from the dihedral angle and hydrogen bond geometry obtained from the calculated structural ensembles and not from the original data. This approach enabled the combination of all structural information to contribute to the geometrical characteristics of each peptide. The helix associated residues for each peptide were identified as Ala10-Thr14 for A20FMDV1; Leu10-Val17 for A20FMDV2 and Leu10-Gly15 for A20LAP.

40 structure ensembles for A20FMDV1, A20LAP and A20FMDV2 are shown in FIG. 5. All three peptides show a similar structure, with the RGD sequence forming the head of a loop which is followed immediately by a helical region. The Arginine and Aspartate residues point outwards from the loop, forming a kind of hammerhead similar to that observed in the crystal structure of αvβ3 bound to an RGD peptide (Xiong et al, 2002). The helical region varies in length between the three peptides. A20FMDV2 has the greatest degree of ordered structure (FIGS. 5E & F) and the longest helix, containing approximately three turns. A20LAP has a slightly shorter helix and A20FMDV1 has a very short helix, consisting of only one turn. Thus helical structure in the LXXL/I region correlates with biological anti-αvβ6 activity.

Thus, NMR analysis confirmed CD data that all three peptides had helices in their structure and that the location of this extended α-helical element was directly C-terminal to the RGD motif. Residue i-j contacts, as shown for NH-NH in FIG. 3, identifies constraints that make all three peptides adopt a turn conformation that enables the RGD motif to be presented at the turn of a hairpin structure. Long-range contacts were observed between Ala3-Thr17 and Ser4-Thr15 for A20FMDV; Val3-Arg19, Val3-Thr20, Pro4-Val17, Leu6-Val12 and Gly8-Val12 for A20FMDV-2 and Pro2-Ala11, Pro2-Ile13, Pro2-His14, Thr4-Ala11 and Gly5-His14 for A20LAP.

Saturation Transfer Difference NMR

Figure 3:
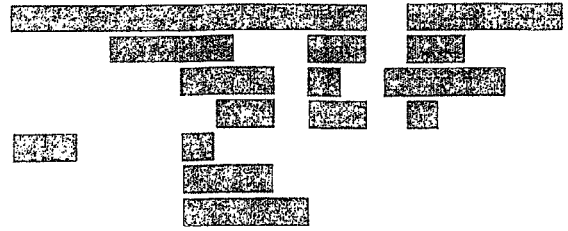
FIG. 3. Schematic of main NOE and ROE contact types, hydrogen bond acceptors and residues giving rise to f restraints for (a) A20FMDV1 (SEQ ID NO: 7), (b) A20FMDV2 (SEQ ID NO: 8) and (c) A20LAP (SEQ ID NO: 6).
Figure 3:
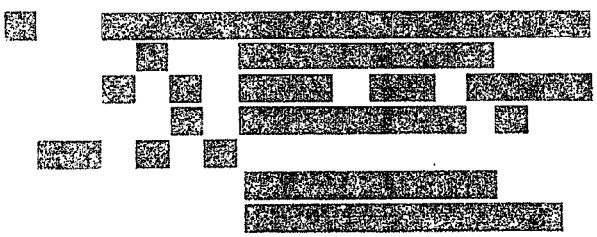
Figure 3:
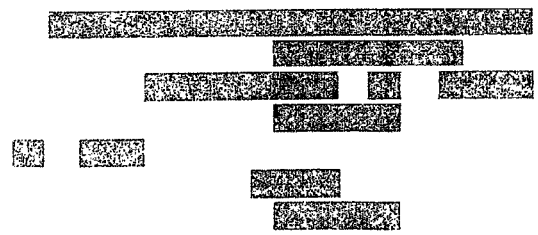

It is clear that the length of the α-helices C-terminal to the RGD motif in the three 20 mer peptides, increases with increasing efficacy of the peptides (see FIG. 3). These data suggest that the length or stability of the helix may contribute to the potency of the peptides to function as αvβ6 antagonists. However, the NMR identification of an α-helix C-terminal to RGD in our peptides was performed in the presence of a helix stabilizing solvent, TFE. To determine whether the peptides are in the form of a helix when associated with αvβ6 in physiological buffer we utilized saturation transfer difference NMR. STD NMR spectra identifying the interactions of the most potent αvβ6 antagonist peptide, A20FMDV2, with the integrin αvβ6 are shown in FIG. 6. Analysis of the STD difference spectrum was made possible by the reasonable dispersion of NMR resonances in this peptide in the absence of TFE. Where degenerate chemical shifts created overlap, any STD difference values were attributed equally to both nuclei in order to remove any potential bias from the data.

Control 1H STDNMR spectra FIG. 6(a) and FIG. 6(c) highlight all 1H NMR resonances from the peptide and STD difference spectra shown in FIGS. 6(b) and 6(d) highlight those 1H resonances that have been in proximity to the integrin during the binding event. FIGS. 6(c) and 6(d) enable the identification of key contact points including Hd and Hb of Leu13 and Leu10 as well as Arg7 Hb/Hd, Thr20 Hg and Lys16 Hb/Hd. Key resonances illustrating reduced or absent STD difference spectra included Leu6 Hd and Hg of Gln11, Val12 and Gln15 and Val17. STD amplification factors for individual nuclei were calculated from this data to be from 0.0 to 8.81 with residue sum amplification factors observed for all residues in A20FMDV2. The relative STD amplification factor across all residues of A20FMDV2 are shown in FIG. 7 and identifies that contact is highlighted across the entire peptide with major interactions observed for Arg7, Asp9, Leu10, Val12, Leu13, Lys16, Val17 and Thr20. These data may suggest that contacts beyond the DLXXL/I helical motif are important for improved binding to αvβ6.

Presence of Helical Structure in αvβ6-Bound Peptide

The presence of the helix causes the non-consecutive leucine and leucine/isoleucine residues of the DLXXL/I motif to be brought into juxtaposition, thus forming a small hydrophobic patch. Since interactions between hydrophobic patches are one of the classic mechanisms for protein-protein binding, it is possible to hypothesise that the Leucine-Leucine or Leucine-Isoleucine patch brought about by the helix is involved directly in binding of the peptides to αvβ6. This would explain why the identity of the 'XX' residues is less important than the leucine and leucine/isoleucine residues in the DLXXL/I motif (Kraft et al, 1999). In order to test this hypothesis we employed Saturation Transfer Difference (STD) NMR, a technique which measures energy transfer from a large protein, in this case rsαvβ6, to a much smaller molecule, in this case the peptide A20FMDV2. The technique works on an atom-specific basis and gives a measurement of proximity of individual residues in a small ligand (A20FMDV2) to a large, receptor protein (rsαvβ6). In this way it is possible to gain an indication of the precise residues involved in binding of the peptide to the receptor. Excluding Arg$^1$, which as part of the RGD motif is expected to exhibit strong contacts with αvβ6, the residues with the highest levels of energy transfer are Leu$^{10}$, Leu$^{13}$, Lys$^{16}$ and Val$^{17}$; thus major contacts with αvβ6 have a regular periodicity of approximately three residues. This is strongly indicative of the presence of helical structure on binding. It is important to note that, unlike the solution NMR experiments, the STD NMR was carried out in physiological buffer (PBS) and in the absence of the helix-stabilising alcohol TFE. Therefore this is strong evidence that although A20FMDV2 exists in solution in equilibrium between helical and random-coil states, the αvβ6-bound peptide exists in a predominantly helical state. Indeed, when the residues that show the highest degree of close contact with αvβ6 are mapped onto the mean 3-dimensional structure of A20FMDV2 in 30% TFE, these residues align on a single face of the peptide. This strongly indicates that the presence of helical structure brings these otherwise non-adjacent residues into juxtaposition, forming a single binding-face for direct interaction with αvβ6.

An α-Helix is Required for Optimal Binding to αvβ6

The data above shows clearly that when A20FMDV2 binds to αvβ6 there is an α-helix C-terminal to RGD. Moreover, by bringing into juxtaposition the two non-contiguous leucines at L10 and L13 this allows for a close contact between the ligand (A20 FMDV2) and the integrin. In order to prove that the α-helix was required for ligand binding to αvβ6, we synthesized three A20 FMDV2 variant peptides that replaced L-valines with D-valines at positions D12 and D17. FIG. 4 shows that each of these valines is predicted to be within the α-helix formed by A20FMDV2, which was confirmed by NMR. By inserting D-valines, we would expect to disrupt the helical nature of the peptide without removing the possibility of key contact residues (Arg7, Asp9, Leu10 and Leu13) from interacting, while maintaining other aspects of the peptide, such as charge distribution and pH.

The D-Valine peptides were analysed in cell adhesion assays with 3T3β6.19 and VB6 cell lines and the data summarised in the table below. The results indicate that the L-to-D changes have a cumulative effect: while peptides DV12 and DV17 have IC50s approximately three times higher than that of 'parent' peptide A20FMDV2, the efficacy of DV1217 is reduced by approximately 20-fold in VB6 assays and 40-fold in the 3T3β6.19 assays, see the table below.

TABLE 7

IC50 values for D-Valine-containing peptides in cell adhesion assays.

| Peptide | 3T3β6.19 | | | VB6 | | |
|---|---|---|---|---|---|---|
| | IC50 (μM) | SD (μM) | n | IC50 (μM) | SD (μM) | n |
| A20FMDV2 | 1.2 | 0.2 | 4 | 0.96 | 0.16 | 3 |
| DV12 | ND | ND | 0 | 3.35 | 0.65 | 3 |
| DV17 | ND | ND | 0 | 2.97 | 2.02 | 3 |
| DV1217 | 48.5 | 37 | 4 | 22.81 | N/A | 2 |

SD, standard deviation; n, number of experiments; ND, not determined.

Peptide DV1217 was also compared to A20FMDV1, A20LAP and A20FMDV2 in an isolated receptor binding assay, using peptides synthesised with an N-terminal biotin. Briefly, 96-well plates were coated with rsαvβ6 and remaining non-specific protein binding sites blocked by incubation with 1% (w/v) casein in PBS. Wells were incubated with biotinylated peptides before washing and subsequent detection of bound peptide with ExtrAvidin HRP. Biotinylated peptides bound specifically to immobilised rsαvβ6, as there was no binding in the absence of rsαvβ6. Binding was sequence-specific, as control peptides with scrambled sequences bound very little in comparison with the original sequences, and showed no binding at all at concentrations below 100 nM. Peptide A20FMDV2 showed a higher degree of binding to αvβ6 than A20LAP, and both bound more than A20FMDV1. Peptide DV1217, which except for the isomerism of D-Val$^{12}$ and D-Val$^{17}$ and consequent lack of helical structure is chemically identical to A20FMDV2, only bound as well as A20FMDV1. Thus, helical structure correlates with binding to rsαvβ6 in isolated protein assays as well as in inhibition of cell adhesion assays. These data also show that while the presence of helical structure promotes binding to αvβ6, the potential to form helical structure is not a pre-requisite for binding; as evidenced by the dose-dependent binding of A20 DV1217.

To confirm that the D-valine substitutions had in fact disrupted helix formation we analysed the double-mutant by CD and NMR. The CD data show that the DV1217 mutant was unable to form a helix even in 50% TFE and the NMR analysis that helix formation was not predicted from 40 overlapping ensembles. Since there were only structural differences, no sequence or charge differences between A20 FMDV2 and the DV1217 double mutant, these data suggests strongly that an α-helix C-terminal to RGD is an essential component of an optimal αvβ6-specific binding motif.

P18-INK6 Derived Peptides

Whereas A20FMDV1, A20FMDV2 and A20LAP peptides were derived from protein sequences that are known to bind integrin αvβ6, we investigated whether other sequences that contain the RGDLXXL/I (SEQ ID NO: 1/SEQ ID NO: 2) sequence motif whereby the LXXL/I motif is contained within an alpha-helical structure. We chose the motif contained in the P18-INK6 gene (also known as Cyclin-dependant kinase 4 inhibitor C or P18-INK4c) with sequence shown below.

```
DD19
                                       (SEQ ID NO: 12)
VPNLRGDLQVLA

P18-INK
                                       (SEQ ID NO: 13)
SAAARGDLEQLTSLLQNNVNV
```

The P18-INK sequence contains the RGDLXXL (SEQ ID NO: 1) sequence and when analysed using the AGADIR software and showed that the LEQL sequence in P18-INK peptide formed an alpha-helical motif. This sequence would therefore be predicted to have αvβ6-binding properties, despite the limited likelihood of this being a physiological interaction because the αvβ6 ligand-binding site is extracellular while p18-INK6 is intracellular.

Comparison of the binding affinity of the P18-INK with that of DD19 (a RGDLXXL (SEQ ID NO: 1) peptide with LXXL sequence not in an alpha helical structure) to integrin αvβ6 showed that the binding affinity of P18-INK was significantly greater than that of DD19 (FIG. 8). This indicates that RGDLXXL (SEQ ID NO: 1) sequences which are contained in proteins not known to bind αvβ6 but which contain the LXXL motif as part of an alpha-helix still bind αvβ6 when presented in isolation.

In Silico Modelling of P-INK Peptides Using AGADIR

In addition, it was decided to use this system to explore the possibility of using in silico design (via the AGADIR algorithm) to enhance peptide helicity, and thereby potentially enhance anti-αvβ6 potency. Different ways of combining the A20FMDV2 and p18-INK sequences were looked at, and the one which gave the highest degree of predicted helicity in the LXXLXX region (INK-FMDV) was chosen for further study. Subsequently, two more peptides were made, with single amino acid changes: the first, INK-FMDV-X, increased the overall predicted helicity of the peptide; the second, pINK-FMDV2-XX, increased the predicted helicity of the LXXLXX region while decreasing the predicted helicity of the RGD.

These peptides were analysed using the Screening ELISA. Briefly, rsαvβ6 was immobilised on the surface of 96-well plates by exposure to plates coated with an anti-αv monoclonal antibody (P2W7). The immobilised rsαvβ6 was then exposed to a mixture of peptide and biotinylated-fibronectin for one hour, after which unbound material was washed away and bound biotinylated-fibronectin detected with ExtrAvidin-HRP. Serial dilutions of peptide allowed the generation of a dose-response curve, from which an IC50 was calculated using a sigmoidal curve-fit model (Prism software).

The results showed that a 20 mer peptide derived from the p18-INK6 sequence is a functional inhibitor of recombinant αvβ6, with an IC50 of 23 nM in competitive ELISA. The peptide P-INK also inhibited αvβ6-dependent adhesion in a preliminary cell adhesion assay.

Peptides derived from the intracellular protein p18-INK6 are therefore capable of inhibiting recombinant and cellular αvβ6. This is unlikely to have a physiological impact as the ligand-binding domain of αvβ6 is extracellular and therefore unlikely ever to 'see' p18-INK6; however these data lend support to the model proposed here, that an RGDLXXL (SEQ ID NO: 1) motif with a helical tendency in the LXXL region is likely to possess αvβ6-binding activity.

Assessment of Peptide Specificity by Flow Cytometry

Biotinylated peptides were allowed to bind to A375Ppuro and A375Pβ6puro and binding detected with a mouse anti-biotin antibody followed by AlexaFluor488-conjugated goat anti-mouse. The use of a secondary antibody that bound biotin provided an important amplification step, as preliminary experiments using direct detection with streptavidin-FITC resulted in little or no detectable signal. The peptides were tested at several different concentrations and demonstrated concentration-specific differential binding to the A375Pβ6puro cell line. DV1217 was highly specific for A375Pβ6puro, as it did not bind noticeably to A375Ppuro at any of the concentrations tested (up to 100 μM), but bound to A375Pβ6 at 10 μM and at 1 μM. A20FMDV2 did bind to A375Ppuro, but only at 10 μM, whereas binding to A375Pβ6puro was observed at 10 μM, 1 μM, 0.1 μM, 0.01 μM and 0.001 μM; differential binding of four orders of magnitude. A20FMDV1 was also relatively specific, showing binding to A375Pβ6puro at 1 μM, a concentration at which it did not bind to A375Ppuro. A20LAP showed relatively little specificity for A375Pβ6puro and bound to both cell lines at 10 μM and 1 μM, although binding to A375Pβ6puro was slightly greater at both concentrations.

All the peptides contained an RGDLXXL/I (SEQ ID NO: 1/SEQ ID NO: 2) motif; therefore the presence of this motif is not a guarantee of specificity for αvβ6. In addition, of the four peptides tested, the two peptides with the most stable (A20FMDV2) and the least stable (A20DV1217) helices in the post-RGD sequence were the most specific for αvβ6 over the other RGD-directed integrins present; therefore helicity in the post-RGD region does not provide specificity for αvβ6. However, these data do confirm the importance of post-RGD helicity for high affinity binding to αvβ6, as 10 μM A20 DV1217 was required in order to obtain a similar degree of binding as 10 nM A20FMDV2. In this assay therefore, loss of helicity resulted in a 1000-fold loss of anti-αvβ6 potency.

Rational Design of Disulphide-Cyclic Derivatives of A20FMDV2

We though that as linear peptides may sometimes be susceptible to attack by serum proteases in vivo, that the cyclisation and use of D-amino acids could be investigated to stabilise the peptides while maintaining, or improving, their biological activity (Okarvi, 2004). Rational, structure-guided design was therefore used to derive two disulphide-cyclised variants of lead peptide A20FMDV2. The aim was three-fold: to stabilise the active structure, thereby increasing the affinity; to improve resistance to serum proteases; and to introduce suitably positioned lysine and tyrosine residues to allow direct radiolabelling with 4-[$^{18}$F]-fluorobenzoic acid ($^{18}$F-FBA) or $^{125}$I, respectively.

Disulphide By Design software (Dombkowski, 2003; www.ehscenter.org/dbd/) was used with the solution structure of A20FMDV2 in 30% TFE to identify a pair of residues which were considered to meet spatial and geometrical specifications for possible replacement with disulphide-bonded cysteine residues. Lysine and tyrosine residues were added for radiolabelling. However, in order to maintain the entire structural unit of A20FMDV2 and prevent possible interference with the αvβ6-binding activity, these residues were added at the N-terminus of the peptide as a D-amino acid 'tail'. This peptide was designated DBD1 (see the table below). Ironically, preliminary serum stability studies indicated that the D-amino acid 'tail' may itself be susceptible to proteolysis. Peptide DBD2 was therefore designed in which all residues are contained within the disulphide ring (Table 6.1). Peptide 'Ran' was synthesised as a control and consists of the same residues as DBD1; however the residues within the disulphide ring have been scrambled.

In order to allow direct analysis of peptide binding to cellular and recombinant αvβ6, a biotin moiety and spacer was also added to the N-terminus of each peptide (biotinylated-A20FMDV2, -DBD1, -Ran and -DBD2 are thus referred to as B-A20FMDV2, B-DBD1, B-Ran and B-DBD2).

TABLE 8

Sequences of cyclic and control peptides Residues in lower case represent D-amino acids. The RGDLXXL (SEQ ID NO: 1) motif is underlined. Cysteine residues used for cyclisation are highlighted in bold and are underlined. Tyrosine (y/Y) and lysine (k/K) residues added to enable direct radiolabelling with $^{125}$I and $^{18}$F-lysine (K) residues added to potentially enable Fluorobenzoic acid respectively. Glutamic acid (e) and side-chain-to-side-chain covalent cyclisation.

|  | Sequence (SEQ ID NO) | Modifications |
|---|---|---|
| A20FMDV2 | NAVPNLRGDLQVLAQKVART (8) | None |
| DBD1 | eykCPNLRGDLQVLAQKVCRTK (14) | Disulphide-cyclised |
| Ran | eykCKLVGALQPDNVLQRCRTK (15) | Disulphide-cyclised |
| DBD2 | CYVPNLRGDLQVLAQKVAKC (16) | Disulphide-cyclised |

Affinity and Specificity of Cyclic Peptides In Vitro

Affinity of the cyclic peptides for αvβ6 was first tested in a non-competitive binding ELISA. Biotinylated peptides were allowed to bind rsαvβ6 immobilised on ELISA plates and bound peptide detected with peroxidase-conjugated ExtrAvidin. The scrambled peptide B-Ran did not show any binding, but both B-DBD1 and B-DBD2 showed concentration-dependent binding to rsαvβ6. Levels of binding were similar to those of B-A20FMDV2. Quantitation of the data by fitting of a dose-response curve and subsequent calculation of the peptide concentrations required for 50% binding (EC50) demonstrated that B-A20FMDV2, B-DBD1 and B-DBD2 exhibit similar levels of potency in this assay, consistently showing detectable binding at low nanomolar concentrations (see Table below).

TABLE 9

EC50s for binding of biotinylated cyclic peptides to immobilised rsαvβ6. Data were fitted to a sigmoidal dose-response curve and the peptide concentration required for 50% maximal binding (EC50) determined for each peptide. Data represent the mean and standard deviation of the EC50s from four independent experiments.

| Peptide | Mean EC50 (nM) | Standard Deviation |
|---|---|---|
| B-Ran | ND | ND |
| B-A20FMDV2 | 1.20 | 0.28 |
| B-DBD1 | 0.69 | 0.18 |
| B-DBD2 | 1.70 | 1.16 |

ND, not determined.

Peptide specificity for αvβ6 was assessed by comparison of binding to paired αvβ6-positive and αvβ6-negative cell lines A375Pβ6 and A375Ppuro (FIGS. 9 and 10). Both cell lines express integrins αvβ3, αvβ5, αvβ8 and α5β1 at comparable levels, however only A375Pβ6 expresses αvβ6. Binding of biotinylated peptides was assessed by flow cytometry. B-A20FMDV2, B-DBD1 and B-DBD2 showed concentration-dependent binding to A375Pβ6, with high levels of binding at concentrations as low as 1 nM. In contrast, these three peptides exhibited only low levels of binding to A375Ppuro, and then only at high concentrations. The control scrambled peptide (B-Ran) did not bind to either cell line.

In order to confirm the specificity of the interaction with A375Pβ6, binding of 1 nM peptide was assessed in the presence of either 63G9, an αvβ6-specific function-blocking monoclonal antibody, or an irrelevant IgG control. B-A20FMDV2, B-DBD1 and B-DBD2 bound strongly in the presence of control IgG; however in the presence of 63G9, binding was greatly reduced, and in the case of B-A20FMDV2 and B-DBD2, completely abolished. B-Ran did not bind in the presence of either antibody. The results confirm that at 1 nM, B-A20FMDV2, B-DBD1 and B-DBD2 bind to A375Pβ6 primarily through αvβ6. Thus B-A20FMDV2, B-DB1 and B-DBD2 have both high affinity and high specificity for αvβ6 over αvβ3, αvβ5, αvβ8 and α5β1. In addition, peptide binding is stable and long-lived, as the peptide-integrin complexes are stable to repeated treatment with EDTA.

In Vivo and In Vitro Studies with $^{18}$F-Labelled A20FMDV2 and DBD2

Lead peptides B-A20FMDV2 and B-DBD2 therefore exhibit high affinity and high specificity for αvβ6 in vitro. A20FMDV2 and DBD2 can be radiolabelled at the N-terminus of the peptide to generate $^{18}$F-A20FMDV2 and $^{18}$F-DBD2). The potential use of integrin αvβ6 for imaging and targeting purposes can be assessed by injection of labelled peptides (with F$^{18}$ or other radioactive moiety) into mice bearing paired αvβ6-positive (DX3β6) and αvβ6-negative (DX3puro) xenografts to allow specific visualisation of the αvβ6-positive tumours.

Discussion

The integrin αvβ6 is a major new target for the imaging and therapy of cancer. As a step toward creating anti-αvβ6 reagents we used a rational design approach based on known ligands of αvβ6 to generate peptide antagonists to αvβ6. These studies have revealed the structural basis of novel integrin-ligand interactions that are important for the biological behaviour of αvβ6. We first noted that the potency of peptide antagonists to αvβ6 increased with increasing length of peptide suggesting secondary structure in these linear peptides. The possibility that our peptides may have a helical motif was based on the crystal structure of FMDV (Logan et al 1993). These authors showed that the G-H loop of the VP1 capsid protein of FMDV consisted of an RGD motif at the tip of a hairpin turn followed by a $3_{10}$ helix. This structure was revealed only if di-sulphide cysteine crosslinking between the VP1 and VP2 proteins was present. We examined the helical propensity of our three lead peptides A20 FMDV1, A20 FMDV2 and A20 LAP using AGADIR software. The prediction was that there was an increasing helical propensity in the order A20FMDV<A20LAP<A20FMDV2, a sequence that correlated with biological potency. Far UV/CD analysis confirmed that all the 20 mers showed an increased helical nature upon addition of TFE from 0-50% (v/v). The wider profile for transition to the helical form for A20FMDV suggests that a higher proportion of TFE is required with this peptide to form a stable helix and that helical propensity of this peptide is lower than for A20FMDV2 or A20LAP data that confirms the AGADIR prediction. The FarUV-CD data also was used to predict what concentration of TFE was needed to obtain comparative structures of all three peptides by NMR. The mean elipticity plot suggested that at 40-50% TFE stabilization of the helix was forced to completion for all 3 peptides. Thus a concentration of 30% (v/v) was used as it lay at the edge of transition for both A20FMDV2 and A20LAP and allowed for differences in helical propensity of the peptides to be revealed. (To allow direct comparison, 30% TFE was also chosen for all subsequent NMR analysis).

Structural assignment of all three peptides by NMR enabled the identification of over 97% of all resonances with the majority of absent resonances from Thr2 of A20FMDV1 and Gly1 from A20LAP being difficult to assign as a result of amide hydrogen exchange and overlap. The high degree of assignment enabled precise contact assignments for structure elucidation of each peptide and the evaluation and documentation of key contacts involved in the formation of α-helices as shown in FIG. 3 and FIG. 4. Contacts shown in FIG. 3(a) for A20FMDV highlight that this helix is the least defined under the conditions used. aH-NH i-i+3 and aH-bH i-i+3 are not continuously defined throughout the region C-terminal to RGD and the helical stretch from Ala10-Thr14 is not defined with hydrogen bond acceptors and f restraints. In contrast, A20FMDV2 contacts as shown in FIG. 3(b) highlight a well formed helix from Leu10-Val17 with aH-NH i-i+3, aH-bH i-i+3, NH-NH i-i+1 and hydrogen bond and f restraints. A20LAP constraints in FIG. 3(c) falls in between those observed for A20FMDV and A20FMDV2. Over the helical region of Leu10-Gly15, A20LAP has a high degree of aH-NH i-i+3 contacts defined but a poorer number of aH-bH i-i+3 contacts defined. Also in A20LAP, the hydrogen bond and f restraints are better defined at the N-terminal end of the helix but are absent in the C-terminal section. The shortfall in the defined hydrogen bond and f restraints for both A20FMDV1 and A20LAP have contributed to the reduction in helix formation in the NMR data created models but reflects the fundamental differences between these peptides in 30% TFE (v/v). The scale of helicity afforded from the contact data where ideal helicity is observed by A20FMDV2, with A20LAP somewhat less ideal and A20FMDV1 being poor can also be seen directly from the experimental data as shown in FIG. 4. A20FMDV2 data in FIGS. 4(b), 4(e) and (4h) shows more contacts and higher dispersion of signals that are indicative of structure being present. Once again, these observations are reduced in A20LAP with the number of contacts and dispersion being the lowest in A20FMDV. Contact data from Table 2 confirms these visual observations. Regardless of the nature of these helices, it is clear that each peptide adopts a turn conformation and that long distance contacts (i.e. between residues in the N- and C-terminal halves of the peptides) are observed in all peptides. These contacts are most numerous and well defined in A20FMDV2 and suggest that helix formation is key to forming a stable turn conformation. However, even though the N-terminal 6-7 amino acids appear not to have structure, they may still be important from activity considerations since there are a number of NOE interactions between and N- and C-terminal residues that likely serve to stabilize the overall 3D structure.

Figure 1:
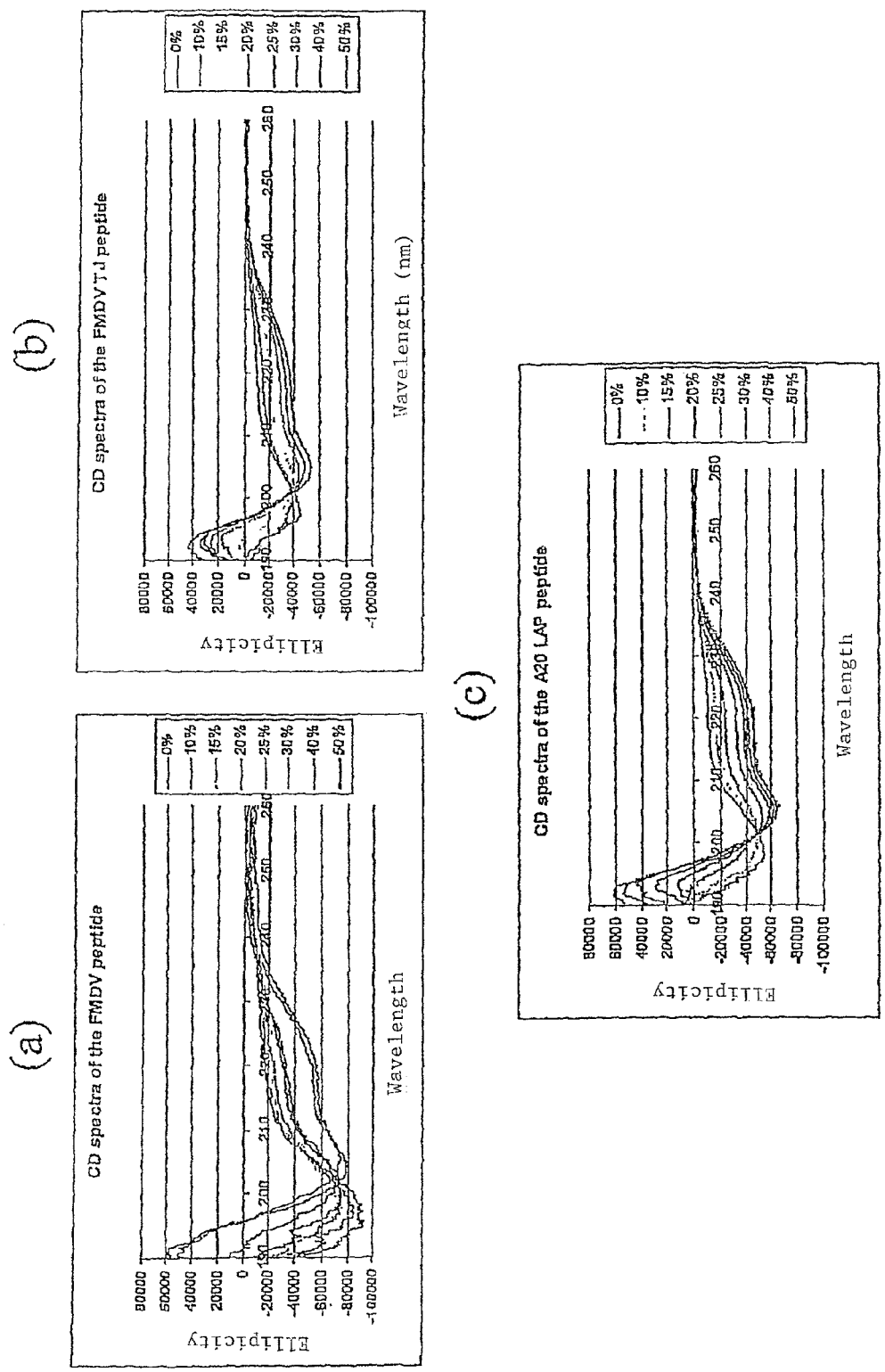
FIG. 1. FarUV-CD Spectra of (A) A20FMDV1, (B) A20FMDV2 and (C) A20LAP peptides in PBS with TFE concentrations between 0-50% (v/v).

The trend in overall helicity for each of these peptides (A20FMDV2>>A20LAP>>A20FMDV1) as outlined from the contact data is further supported upon structure elucidation using CNS software. The structural information has allowed quantitative analysis of the helical propensity of these peptides in a way that was not immediately clear from the FarUV-CD data presented in FIG. 1 and FIG. 2. Ensemble averages in FIG. 5 show that for each peptide there is a helical section that lies directly C-terminal to the RGD motif. The helix is shown to be approximately 1.4, 1.6 and 2.2 turns for A20 FMDV1, A20 LAP and A20 FMDV2 respectively and appear to agree with the trend observed from AGADIR regarding the overall predicted helicities of these peptides. The nature of the helix that forms directly following the RGD motif enables the side chains of the previously highlighted residues LXX[L/I] to protrude from one side of the helix. As a result, this would create a structural motif involving a helix that is not dissimilar to the LXXLL motif recently illustrated that binds peroxisome proliferator-activator receptor (PPAR) (Klien et al, 2005). The RGDLXXL (SEQ ID NO: 1) sequence was identified as an αvβ6-specific motif by Kraft et al (1999) using peptide phage display and the importance of these residues was discovered in earlier studies that examined the critical amino-acids in FMDV derived peptides that were required to inhibit experimental infection by FMDV (Mateu et al, 1996).

Our STDNMR investigation using A20FMDV2 peptide with integrin αvβ6 enabled the confirmation that residues LXXL were important in ligand binding to αvβ6. The STDNMR difference data shown in FIG. 6 highlights the importance of interactions through the Hd of residues Leu10 and Leu13 together with the absence of Hd of Leu6 highlights immediately that binding primarily involves the section of the peptide from Arg7-Thr20. This is confirmed by analysis of the STD amplification factor shown for each residue that also highlights that the primary interface occurs with residues Arg7, Leu10, Leu13, Lys16 and Val17. Thus our data provide a structural explanation for the discovery of RGDLXXL (SEQ ID NO: 1) as an αvβ6-specific ligand since the helix brings into juxtaposition the non-contiguous Leu10 and Leu13 residues which the interact with the αvβ6 surface in a linear fashion. The significance of residues Lys16 and Val17 in integrin αvβ6 recognition also requires attention as this observation highlights the likely importance of an extended motif beyond RGDLXXL (SEQ ID NO: 1). Secondary elevated interactions are also observed for Asp9, Val12 and Thr20. Since the STD data was obtained in a physiological buffer (PBS) without TFE, it suggests strongly that A20FMDV2 binds as a helix to αvβ6. The primary interface residues occurring in steps of three amino acids illustrate the formation of a helix within A20FMDV2 during interaction with αvβ6 that would enable all primary residue side chains to interact as one face with the integrin target. Furthermore, it is possible that at least the N-terminal section of the helix between Leu10-Lys16 could adopt a 3,10-helix structure due to the LXXLXXK regular pattern in agreement with Logan et al (1993). Our data suggest that peptides specific to integrin αvβ6 require an extended turn conformation with an RGDLXXL (SEQ ID NO: 1) based motif. In addition to the immediate importance of this motif, αvβ6 specific peptides require increased helical propensity and the ability to form helices with increasing numbers of residues C-terminal to RGD will bind with greater efficacy.

This was, perhaps, an unexpected finding since development of peptide inhibitors to other integrins such as αvβ3 and αIIbb3 have often striven for the smallest possible cyclic peptide. The α-helix motif for αvβ6 appears to have several roles. Primarily, it allows correct orientation of the LXXL to enable hydrophobic side chains to interact with a binding site on αvβ6, but in addition it promotes binding by also presenting contact residues in positions YY in an extended sequence RGDLXXLXXYY (SEQ ID NO: 17). Moreover, the long range contacts between residues in the helix and residues in the N-terminus stabilize the hairpin structure and thus present the RGD motif favourably.

The combination of structural (NMR and far UV/CD analysis) and functional (ELISA and adhesion assays) data predicted that our peptides antagonists assumed a helical component when they interacted with αvβ6. This was confirmed for A20 FMDV2/αvβ6 interaction by STDNMR. The importance of the helix in peptide binding to αvβ6 was shown by conservatively destroying the helix by replacing valines in the helix with their D-isomers. The resultant DV1217 peptide had no helical propensity and a 20-40 fold reduced potency as an αvβ6 inhibitor.

Some substrates, such as fibronectin, are not predicted to have an α-helix C-terminal to RGD but can function as ligands for αvβ6. However, αvβ6 has a much greater affinity of binding for LAP than for fibronectin. Since LAP possess an RGD-α-helix motif our results offer a structural explanation for this increased affinity since, presumably, there are more physical interactions between αvβ6 and LAP than with αvβ6 and fibronectin. Our data may also explain how αvβ6 can activate TGFβ. Thus activation of TGFβ1 (and presumably TGFβ3) by αvβ6 requires a functional actin cytoskeleton possibly suggesting that physical tension must be applied to the TGFβ-propeptide, LAP. The large number of contact sites that occur C-terminal to the RGD binding motif in our peptides offer an explanation as to how this strong binding to LAP could be mediated. This may be αvβ6 activation of TGFβ through strong, helix-mediated binding, involving traction/tension, or possibly the binding-induced stabilisation from unstructured loop to helix cause a conformational change in the LAP that releases TGFβ.

The RGDLXXL (SEQ ID NO: 1) motif is found in many proteins not all of which are extracellular proteins. Based on these investigations it may be suggested that new, yet uncharacterised, ligands exist for αvβ6, which may include, for example, rhesus macaque pulmonary surfactant associated protein C. The presence of intracellular proteins with RGDLXXL (SEQ ID NO: 1) motifs may suggest that they may bind to intracellular αvβ6, which might be of biological use.

In summary, the 20 mer peptide A20 FMDV2 forms an α-helix C-terminal to RGD when it associates with the integrin. Since there is a correlation between helical-propensity and peptide efficacy, this suggests that helix formation is not a consequence of binding to αvβ6 but rather that the ligand (A20FMDV2) must assume an α-helix C-terminal to RGD before binding and that this binding is likely to stabilize the helix. A major function of the helix is to allow non-contiguous residues C-terminal to the RGD motif to be presented as a linear face to the surface of αvβ6 thereby increasing the potential contact points between the ligand and the integrin. These data will serve as a structural framework upon which to design potent αvβ6-specific reagents that will be required for the imaging and therapy of cancer as well as the treatment of some fibrotic diseases.

REFERENCES

All publications, patent and patent applications cited herein or filed with this application, including references filed as part of an Information Disclosure Statement are incorporated by reference in their entirety.

Brunger et al, (1998) Acta Crystallogr. D Biol. Crystallogr., 54 (Pt 5), 905-921.
Cavanagh, J., Fairbrother, W. J., Palmer, A. G., and Skelton, N. J. (1996) Protein NMR Spectroscopy: Principles and Practice, Academic Press, London.
Delaglio et al, (1995) J. Biomol. NMR 6, 277-293.
Forood et al, (1993) "Stabilization of α-helical structures in short peptides via end capping." Proc. Natl Acad. Sci. 90: 838-842.
Guex & Peitsch, (1997) Electrophoresis 18, 2714-2723.
Johnson & Blevins, (1994) Journal of Biomolecular NMR 4, 603-614.
Klein et al, (2005). J. Biol. Chem. 280, 5682-5692.
Koradi et al, (1996) J. Mol. Graph. 14, 51-55.
Khandelwal et al, Eur. J. Biochem. 264, 468-478.
Laskowski et al, (1996) J Biomol NMR 8, 477-486.
van Gunsteren et al, (1994) in Methods in Enzymology: Nuclear Magnetic Resonance (James, T. L., and Oppenheimer, N. J., eds) Vol. 239, pp. 619-654, Academic Press, New York.
Yan et al, (2003). J. Magn. Reson. 163, 270-276.

TABLE 1

NMR assignment list of observed $^1$H chemical shifts for A20FMDV-1, A20FMDV-2 and A20LAP peptides in PBS/30% (v/v) TFE at 10° C. All chemical shifts are referenced externally to a 100 µM solution of dimethylsilapetane sulphonic acid (DSS) in PBS/30% (v/v) TFE.

| Residue | $H^N$ | $H^\alpha$ | Others |
|---|---|---|---|
| A20FMDV-1 (SEQ ID NO: 7) | | | |
| 1Tyr | 8.336 | 4.341 | $H^{\beta2/\beta3}$ 2.830; $H^{\delta2/\delta3}$ 7.205; $H^{\epsilon1/\epsilon2}$ 6.913 |
| 2Thr | | | |
| 3Ala | 8.615 | 4.350 | $H^\beta$ 1.522 |
| 4Ser | 8.335 | 4.496 | $H^{\beta2/\beta3}$ 4.000, 3.920 |
| 5Ala | 8.426 | 4.415 | $H^\beta$ 1.500 |
| 6Arg | 8.317 | 4.308 | $H^{\beta2/\beta3}$ 1.872, 1.969; $H^{\gamma2/\gamma3}$ 1.706, 1.774; $H^{\delta2/\delta3}$ 3.285 |
| 7Gly | 8.407 | 4.007 | |
| 8Asp | 8.337 | 4.677 | $H^{\beta2/\beta3}$ 3.227, 3.364 |
| 9Leu | 8.245 | 4.286 | $H^{\beta2/\beta3}$ 1.782; $H^\gamma$ 1.722; $H^{\delta1/\delta2}$ 0.941, 0.990 |
| 10Ala | 8.235 | 4.394 | $H^\beta$ 1.328 |
| 11His | 8.226 | 4.604 | $H^{\beta2/\beta3}$ 3.295, 3.394; $H^{\epsilon1}$ 7.275 |
| 12Leu | 8.231 | 4.343 | $H^{\beta2/\beta3}$ 1.862; $H^\gamma$ 1.695; $H^{\delta1/\delta2}$ 0.931, 0.970 |
| 13Thr | 8.276 | 4.386 | $H^\beta$ 4.202; $H^{\gamma2}$ 1.471 |
| 14Thr | 8.148 | 4.323 | $H^\beta$ 4.244; $H^{\gamma2}$ 1.281 |
| 15Thr | 8.246 | 4.347 | $H^{\gamma2}$ 1.474 |
| 16His | 8.312 | 4.762 | $H^{\beta2/\beta3}$ 3.225, 3.343; $H^{\epsilon l}$ 7.145 |
| 17Ala | 8.506 | 4.425 | $H^\beta$ 1.498 |
| 18Arg | 8.278 | 4.392 | $H^{\beta2/\beta3}$ 1.838, 1.917; $H^{\gamma2/\gamma3}$: 1.6791, 1.742; $H^{\delta2/\delta3}$ 3.325 |
| 19His | 8.315 | 4.702 | $H^{\beta2/\beta3}$ 3.302; $H^{\epsilon1}$ 7.140 |
| 20Leu | 8.188 | 4.286 | $H^{\beta2/\beta3}$ 1.688, $H^\gamma$ 1.688; $H^{\delta1/\delta2}$ 0.941, 0.988 |
| A20FMDV-2 (SEQ ID NO: 8) | | | |
| 1Asn | | 4.115 | $H^{\beta2/\beta3}$ 2.912; $H^{\delta21/\delta22}$ 6.912, 7.622 |
| 2Ala | 8.250 | 4.300 | $H^\beta$ 1.394 |
| 3Val | 8.197 | 4.491 | $H^\beta$ 2.197; $H^{\gamma1/\gamma2}$: 1.079 |
| 4Pro | | 4.459 | $H^{\beta2/\beta3}$ 1.961; $H^{\gamma2/\gamma3}$: 2.124; $H^{\delta2/\delta3}$ 3.773, 3.920 |
| 5Asn | 8.605 | 4.810 | $H^{\beta2/\beta3}$ 2.838 3.001; $H^{\delta21/\delta22}$ 6.743, 7.776 |
| 6Leu | 8.140 | 4.387 | $H^{\beta2/\beta3}$ 1.714; $H^\gamma$ 1.714; $H^{\delta1/\delta2}$ 0.906, 0.946 |
| 7Arg | 8.253 | 4.257 | $H^{\beta2/\beta3}$ 1.922, 1.997; $H^{\gamma2/\gamma3}$ 1.717, 1.801; $H^{\delta2/\delta3}$ 3.321 |
| 8Gly | 8.272 | 3.982 | |
| 9Asp | 8.400 | 4.574 | $H^{\beta2/\beta3}$ 2.799 |
| 10Leu | 8.279 | 4.253 | $H^{\beta2/\beta3}$ 1.841, 1.896; $H^\gamma$ 1.681; $H^{\delta1/\delta2}$ 0.955, 1.011 |
| 11Gln | 8.065 | 4.123 | $H^{\beta2/\beta3}$ 2.452, 2.572; $H^{\gamma2/\gamma3}$ 2.284; $H^{\epsilon21/\epsilon22}$ 6.866, 7.510 |
| 12Val | 7.733 | 3.825 | $H^\beta$ 2.310; $H^{\gamma1/\gamma2}$: 1.040, 1.155 |

TABLE 1-continued

NMR assignment list of observed ¹H chemical shifts for
A20FMDV-1, A20FMDV-2 and A20LAP peptides in PBS/30%
(v/v) TFE at 10° C. All chemical shifts are referenced
externally to a 100 μM solution of dimethylsilapetane
sulphonic acid (DSS) in PBS/30% (v/v) TFE.

| Residue | $H^N$ | $H^\alpha$ | Others |
|---|---|---|---|
| 13Leu | 7.987 | 4.149 | $H^{\beta2/\beta3}$ 1.773. $H^\gamma$ 1.867; $H^{\delta1/\delta2}$ 0.966 |
| 14Ala | 8.455 | 4.107 | $H^\beta$ 1.553 |
| 15Gln | 7.823 | 4.192 | $H^{\beta2/\beta3}$ 2.517, 2.659; $H^{\gamma2/\gamma3}$ 2.298; $H^{\epsilon21/\epsilon22}$ 6.870, 7.515 |
| 16Lys | 8.109 | 4.265 | $H^{\beta2/\beta3}$ 1.748, 2.076; $H^{\gamma2/\gamma3}$ 1.659; $H^{\delta2/\delta3}$ 1.540; $H^{\epsilon2/\epsilon3}$ 2.988 |
| 17Val | 8.282 | 4.012 | $H^\beta$ 2.250; $H^{\gamma1/\gamma2}$: 1.025, 1.083 |
| 18Ala | 8.030 | 4.367 | $H^\beta$ 1.562 |
| 19Arg | 7.946 | 4.516 | $H^{\beta2/\beta3}$ 1.927, 2.100; $H^{\gamma2/\gamma3}$ 1.781, 1.849; $H^{\delta2/\delta3}$ 3.283 |
| 20Thr | 7.759 | 4.357 | $H^\beta$ 4.253; $H^{\gamma2}$ 1.297 |
| A20LAP (SEQ ID NO: 6) | | | |
| 1Gly | | | |
| 2Phe | 8.276 | 4.576 | $H^{\beta2/\beta3}$ 3.114, 3.263; $H^{\delta2/\delta3}$ 7.260; $H^{\epsilon1/\epsilon2}$ 7.183; $H^\zeta$ 7.298 |
| 3Thr | 8.208 | 4.407 | $H^\beta$ 4.236; $H^{\gamma2}$ 1.156 |
| 4Thr | 8.110 | 4.314 | $H^\beta$ 4.256; $H^{\gamma2}$ 1.239 |
| 5Gly | 8.433 | 3.920 | |
| 6Arg | 8.254 | 4.362 | $H^{\beta2/\beta3}$ 1.745, 1.868; $H^{\gamma2/\gamma3}$ 1.614 $H^{\delta2/\delta3}$ 3.166 |
| 7Arg | 8.461 | 4.237 | $H^{\beta2/\beta3}$ 1.797, 1.880; $H^{\gamma2/\gamma3}$ 1.661, 1.686; $H^{\delta2/\delta3}$ 3.221 |
| 8Gly | 8.042 | 4.257 | |
| 9Asp | 8.151 | 4.574 | $H^{\beta2/\beta3}$ 2.724 |
| 10Leu | 8.144 | 4.174 | $H^{\beta2/\beta3}$ 1.717; $H^\gamma$ 1.569; $H^{\delta1/\delta2}$ 0.851, 0.915 |
| 11Ala | 8.176 | 4.204 | $H^\beta$ 1.438 |
| 12Thr | 7.880 | 4.188 | $H^\beta$ 4.281; $H^{\gamma2}$ 1.188 |
| 13Ile | 7.920 | 3.984 | $H^\beta$ 1.829; $H^{\gamma12/\gamma13}$ 1.130 $H^{\gamma2}$ 0.778; $H^{\delta1/\delta2}$ 0.890 |
| 14His | 8.292 | 4.329 | $H^{\beta2/\beta3}$ 3.117, 3.274; $H^{\epsilon1}$ 7.295 |
| 15Gly | 8.174 | 3.941 | |
| 16Met | 8.139 | 4.457 | $H^{\beta2/\beta3}$ 2.007, 2.105; $H^{\gamma2/\gamma3}$ 2.517, 2.601; $H^\epsilon$ 2.130 |
| 17Asn | 8.304 | 4.681 | $H^{\beta2/\beta3}$ 2.708, 2.773; $H^{\delta21/\delta22}$ 6.915, 7.650 |
| 18Arg | 8.035 | 4.565 | $H^{\beta2/\beta3}$ 1.657, 1.761; $H^{\gamma2/\gamma3}$ 1.483, 1.563; $H^{\delta2/\delta3}$ 3.097 |
| 19Pro | | 4.400 | $H^{\beta2/\beta3}$ 2.137; $H^{\gamma2/\gamma3}$: 1.944; $H^{\delta2/\delta3}$ 3.515 |
| 20Phe | 7.277 | 4.384 | $H^{\beta2/\beta3}$ 3.051, 3.133; $H^{\delta2/\delta3}$ 7.310; $H^{\epsilon1/\epsilon2}$ 7.383; $H^\zeta$ 7.281 |

TABLE 2

List of NOE, hydrogen bond and torsion angle connectivities
for A20FMDV-1, A20FMDV-2 and A20LAP peptides.

| | | A20FMDV-1 | A20FMDV-2 | A20LAP |
|---|---|---|---|---|
| NOE's | Intra-residue | 17 | 39 | 41 |
| | Sequential | 18 | 31 | 24 |
| | i-i + 2 | 16 | 35 | 36 |
| | i-i + 3 | 12 | 32 | 26 |
| | i-j (>3) | 10 | 40 | 23 |
| | Total | 73 | 177 | 150 |
| Hydrogen Bond Donors | | 3 | 8 | 3 |
| Tortion Angles | $\phi$ | 4 | 10 | 4 |

TABLE 3

Structural Statistics for 35 structure ensembles
of A20FMDV-1, A20FMDV-2 and A20LAP peptides.

| | A20FMDV-1 | A20FMDV-2 | A20LAP |
|---|---|---|---|
| Backbone r.m.s deviation across the ensemble over six residues inclusive of: DLXX(L/I)XX (Å) | 0.65 | 0.59 | 0.63 |
| Energy contributions (kcal mol⁻¹) | | | |
| $E_{NOE}$ | 0.18 ± 0.05 | 0.25 ± 0.06 | 0.20.0 ± 0.04 |
| $E_{dihedral}$ | 0.45 ± 0.06 | 0.91 ± 0.02 | 0.33 ± 0.04 |

TABLE 4

Amino Acid Sequence of peptides D-amino acids are shown in lower case and are
highlighted in bold. All DBD1, DBD2 and Ran peptides contain a disulphide bond
between the two cysteines.

| Series | Name | Sequence (SEQ ID NO) | Number of residues |
|---|---|---|---|
| Initial 7-12mers | DD1 | RRGDLATIH (9) | 9 |
| | DD2 | FTTGRRGDLATI (10) | 12 |
| | DD3 | TGRRGDLATI (11) | 10 |
| | DD4 | GRRGDLA (18) | 7 |
| | DD5 | FTTGRRGDL (19) | 9 |
| | DD6 | LRRGDRPSLRY (20) | 11 |
| | DD7 | LRRGDRPSL (21) | 9 |
| | DD8 | LRRGDRP (22) | 7 |
| | DD9 | GGLRRGDRPSL (23) | 11 |
| | DD10 | GGLRRGDRP (24) | 9 |
| | DD11 | GLRRGDRPSL (25) | 10 |
| | DD12 | RGDRPSL (26) | 7 |
| | DD13 | GGFRRGDRPSL (27) | 11 |
| | DD14 | GSIYDGYYVFPY (28) | 12 |
| | DD15 | NAGRRGDLGSL (29) | 11 |
| | DD16 | GRRGDLGSL (30) | 9 |
| | DD17 | NAGRRGDLGS (31) | 10 |
| | DD18 | NAGRRGDL (32) | 8 |
| | DD19 | VPNLRGDLQVLA (12) | 12 |

TABLE 4-continued

Amino Acid Sequence of peptides D-amino acids are shown in lower case and are highlighted in bold. All DBD1, DBD2 and Ran peptides contain a disulphide bond between the two cysteines.

| Series | Name | Sequence (SEQ ID NO) | Number of residues |
|---|---|---|---|
| A20 series | A20FMDV1 | YTASARGDLAHLTTTHARHL (7) | 20 |
| | A20LAP | GFTTGRRGDIATIHGMNRPF (6) | 20 |
| | A20FMDV2 | NAVPNLRGRLQVLAQKVART (8) | 20 |
| p18-INK series | P_FMDV2 | VPNLRGDLQVLAQKVARTLP (33) | 20 |
| | P_18INK | SAAARGDLEQLTSLLQNNVN (34) | 20 |
| | P_FMDV2-INK | VPNLRGDLQVLTSLLQNNVN (35) | 20 |
| | P_INK-FMDV2 | SAAARGDLEQLAQKVARTLP (36) | 20 |
| | P_INK-FMDV2-X | SAAARGDLEQLRQKVARTLP (37) | 20 |
| | P_INK-FMDV2-XX | SAAARGDLETLRQKVARTLP (38) | 20 |
| D-Valine peptides | A20DV12 | NAVPNLRGDLQvLAQKVART (8) | 20 |
| | A20DV17 | NAVPNLRGDLQVLAQKvART (8) | 20 |
| | A20DV1217 | NAVPNLRGDLQvLAQKvART (8) | 20 |
| Biotinylated peptides | B-A20FMDV1 | Biotin-εAhx-YTASARGDLAHLTTTHARHL (7) | 20 |
| | B-A20FMDV1-Ran | Biotin-εAhx-ARHALTYRTGATHLAHTDSL (39) | 20 |
| | B-A20LAP | Biotin-εAhx-GFTTGRRGDIATIHGMNRPF (6) | 20 |
| | B-A20LAP-Ran | Biotin-εAhx-PGRTFHRFGMGAITRTGNDL (40) | 20 |
| | B-A20FMDV2 | Biotin-εAhx-NAVPNLRGDLQVIAQKVART (8) | 20 |
| | B-A20FMDV2-Ran | Biotin-εAhx-RQLNVDALNVAGVRALKPTQ (41) | 20 |
| 1st generation cyclics | DBD1 | eykCPNLRGDLQVLAQKVCRTK (14) | 22 |
| | B-DBD1 | Biotin-εAhx-eykCPNLRGDLQVLAQKVCRTK (14) | 22 |
| | B-Ran | Biotin-εAhx-eykCKLVGALQPDNVLQRCRTK (15) | 22 |
| 2nd generation cyclic | DBD2 | CYVPNLRGDLQVLAQKVAKC (16) | 20 |
| | B-DBD2 | Biotin-εAhx-CYVPNLRGDLQVLAQKVAKC (16) | 20 |

---

The invention claimed is:

1. A method of treating a cancer in a patient, wherein cells of said cancer overexpress αvβ6, the method comprising administering to a patient in need thereof, a therapeutically effective amount of a peptide or a peptide linked to a therapeutically active moiety, said peptide or linked peptide comprising the sequence motif $B_nRGDLX^5X^6LX^8X^9X^{10}Z_mX_i$ or $B_nRGDLX^5X^6IX^8X^9X^{10}Z_mX_i$, wherein $B_n$ is a sequence of n amino acids each of which is any D- or L-amino acid, $X^5$, $X^6$, $X^8$, $X^9$, and $X^{10}$ each independently represent any amino acid, $Z_m$ is a sequence of m amino acids independently selected from the group consisting of: Glu, Ala, Leu, Met, Gln, Lys, Arg, Val, Ile, Trp, Phe and Asp, $X_i$ is a sequence of i amino acids each of which is any amino acid, n is 6 to 7, m is at least 1, and n, m, and i are selected to make the maximum length of said peptide 20 amino acids, and wherein said therapeutically active moiety is selected from the group consisting of: mechlorethamine, cyclophosphamide, ifosfamide, melphalan, chlorambucil, hexamethylmelamine, thiotepa, busulfan, carmustine, lomustine, semustine, streptozoein, decarbazine dimethyltriazenoimidazolecarboxamide, methotrexate, fluorouracil, floxuridine, cytarabine, mercaptopurine, thioguanine, pentostatin, vinblastine, vincristine, etoposide, teniposide, dactinomycin, daunorubicin, doxorubicin, bleomycin, plicamycin, mitomycin, L-asparaginase, interferon alphenomes, cisplatin, carboplatin, mitoxantrone and antbracycline, hydroxyurea, procarbazine, mitotane, aminoglutethimide, taxol, flutamide, tamoxifen, ricin, abrin, *Pseudomonas* exotoxin, tissue factor, TNFα, IL-2, phosphorus-32, iodine-125, iodine-131, indium-111, rhenium-186, rhenium-188, and yttrium-90.

2. A method of diagnosing a cancer in a patient, wherein cells of said cancer overexpress αvβ6, the method comprising:
   detecting whether αvβ6 integrin is present at a tumor by contacting at least one tumor cell with a peptide comprising the sequence motif $B_nRGDLX^5X^6LX^8X^9X^{10}Z_mX_i$ or $B_nRGDLX^5X^6IX^8X^9X^{10}Z_mX_i$, wherein $B_n$ is a sequence of n amino acids each of which is any D- or L-amino acid, $X^5$, $X^6$, $X^8$, $X^9$, and $X^{10}$ each independently represent any amino acid, $Z_m$ is a sequence of m amino acids independently selected from the group consisting of: Glu, Ala, Leu, Met, Gln, Lys, Arg, Val, Ile, Trp, Phe and Asp, $X_i$ is a sequence of i amino acids each of which is any amino acid, n is 6 to 7, m is at least 1, and n, m, and i are selected to make the maximum length of said peptide 20 amino acids, and detecting binding between αvβ6 integrin and said peptide; and
   diagnosing the patient with a cancer that overexpresses αvβ6 when said binding between αvβ6 integrin and said peptide at the tumor is detected.

3. The method of claim 1, wherein said peptide is selected from the group consisting of A20FMDV2 (SEQ ID NO. 8) and DBD2 (SEQ ID NO: 16), said A20FMDV2 (SEQ ID NO: 8) and DBD2 (SEQ ID NO: 16) being optionally biotinylated.

4. The method of claim 1, wherein said peptide is A20LAP (SEQ ID NO: 6).

5. The method of claim 1, wherein said peptide is A20FMDV2 (SEQ ID NO: 8), said A20FMDV2 (SEQ ID NO: 8) being optionally biotinylated.

6. The method of claim 2, wherein said peptide is selected from the group consisting of A20FMDV2 (SEQ ID NO. 8) and DBD2 (SEQ ID NO: 16), said A20FMDV2 (SEQ ID NO: 8) and DBD2 (SEQ ID NO: 16) being optionally biotinylated.

7. The method of claim 2, wherein said peptide is A20LAP (SEQ ID NO: 6).

8. The method of claim 2, wherein said peptide is A20FMDV2 (SEQ ID NO: 8), said A20FMDV2 (SEQ ID NO: 8) being optionally biotinylated.

9. The method of claim 2, wherein said peptide is linked to a detectable moiety selected from the group consisting of: a radioactive moiety, a Magnetic Resonance Imaging (MRI) spin label, and an optical moiety, and wherein detecting binding between αvβ6 integrin and said peptide comprises detecting said detectable moiety.

10. The method of claim 2, wherein the method further comprises providing the patient with a cancer prognosis, wherein the patient is provided with a prognosis of reduced survival when the presence of αvβ6 integrin at the tumor is detected as compared with survival when the presence of αvβ6 integrin at the tumor has not been detected.

11. A method of imaging epithelial cells that overexpress αvβ6 integrin in the body of a patient, the method comprising:
   administering to the patient a peptide comprising the sequence motif $B_nRGDLX^5X^6LX^8X^9X^{10}Z_mX_i$ or $B_nRGDLX^5X^6IX^8X^9X^{10}Z_mX_i$, wherein $B_n$ is a sequence of n amino acids each of which is any D- or L-amino acid, $X^5$, $X^6$, $X^8$, $X^9$, and $X^{10}$ each independently represent any amino acid, $Z_m$ is a sequence of m amino acids independently selected from the group consisting of: Glu, Ala, Leu, Met, Gln, Lys, Arg, Val, Ile, Trp, Phe and Asp, $X_i$ is a sequence of i amino acids each of which is any amino acid, n is 6 to 7, m is at least 1, and n, m, and i are selected to make the maximum length of said peptide 20 amino acids, wherein said peptide is linked to a detectable moiety selected from the group consisting of: a radioactive moiety, a Magnetic Resonance Imaging (MRI) spin label, and an optical moiety; and
   detecting said detectable moiety to thereby image peptide epithelial cells that overexpress αvβ6 integrin.

12. The method of claim 11, wherein the patient is suffering from a condition selected from the group consisting of: chronic fibrosis, chronic obstructive pulmonary disease (COPD), lung emphysema, chronic wounding skin disease and an epithelial tumor.

13. A method of detecting αvβ6 integrin in a patient, said method comprising:
  a) obtaining a cell sample from a human patient; and
  b) detecting whether αvβ6 integrin is present in the cell sample by contacting the cell sample with a peptide comprising the sequence motif $B_n RGDLX^5 X^6 LX^8 X^9 X^{10} Z_m X_i$ or $B_n RGDLX^5 X^6 IX^8 X^9 X^{10} Z_m X_i$ wherein $B_n$ is a sequence of n amino acids each of which is any D- or L-amino acid, $X^5$, $X^6$, $X^8$, $X^9$, and $X^{10}$ each independently represent any amino acid, $Z_m$ is a sequence of m amino acids independently selected from the group consisting of: Glu, Ala, Leu, Met, Gln, Lys, Arg, Val, Ile, Trp, Phe and Asp, $X_i$ is a sequence of i amino acids each of which is any amino acid, n is 6 to 7, m is at least 1, and n, m, and i are selected to make the maximum length of said peptide 20 amino acids, and detecting binding between αvβ6 integrin and said peptide.

14. The method of claim 13, wherein the cell is a cancer cell.

15. The method of claim 13, wherein said peptide is linked to a detectable moiety selected from the group consisting of: a radioactive moiety, a Magnetic Resonance Imaging (MRI) spin label, and an optical moiety, and wherein detecting binding between αvβ6 integrin and said peptide comprises detecting said detectable moiety.

\* \* \* \* \*

SEQUENCE LISTING

<160> NUMBER OF SEQ ID NOS: 41

<210> SEQ ID NO 1
<211> LENGTH: 7
<212> TYPE: PRT
<213> ORGANISM: Artificial sequence
<220> FEATURE:
<223> OTHER INFORMATION: Synthetic peptide: Sequence motif
<220> FEATURE:
<221> NAME/KEY: misc_feature
<222> LOCATION: (5)..(6)
<223> OTHER INFORMATION: Xaa is any residue
<220> FEATURE:
<221> NAME/KEY: misc_feature
<222> LOCATION: (5)..(6)
<223> OTHER INFORMATION: Preferably, Xaa is a helix promoting residue
<220> FEATURE:
<221> NAME/KEY: misc_feature
<222> LOCATION: (5, 6)
<223> OTHER INFORMATION: Preferably, Xaa is a helix promoting residue
      independently selected from the group consisting of Glu, Ala, Leu,
      Met, Gln, Lys, Arg, Val, Ile, Trp, Phe and Asp

<400> SEQUENCE: 1

Arg Gly Asp Leu Xaa Xaa Leu
1               5

<210> SEQ ID NO 2
<211> LENGTH: 7
<212> TYPE: PRT
<213> ORGANISM: Artificial sequence
<220> FEATURE:
<223> OTHER INFORMATION: Synthetic peptide: Sequence motif
<220> FEATURE:

```
<221> NAME/KEY: misc_feature
<222> LOCATION: (5)..(6)
<223> OTHER INFORMATION: Xaa is any residue
<220> FEATURE:
<221> NAME/KEY: misc_feature
<222> LOCATION: (5)..(6)
<223> OTHER INFORMATION: Preferably, Xaa is a helix promoting residue
<220> FEATURE:
<221> NAME/KEY: misc_feature
<222> LOCATION: (5, 6)
<223> OTHER INFORMATION: Preferably, Xaa is a helix promoting residue
      independently selected from the group consisting of Glu, Ala, Leu,
      Met, Gln, Lys, Arg, Val, Ile, Trp, Phe and Asp

<400> SEQUENCE: 2

Arg Gly Asp Leu Xaa Xaa Ile
1               5

<210> SEQ ID NO 3
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (5, 6, 8..10)
<223> OTHER INFORMATION: Xaa is any residue
<220> FEATURE:
<221> NAME/KEY: misc_feature
<222> LOCATION: (5, 6, 8..10)
<223> OTHER INFORMATION: Preferably, Xaa is a helix promoting residue
<220> FEATURE:
<221> NAME/KEY: misc_feature
<222> LOCATION: (5, 6, 8..10)
<223> OTHER INFORMATION: Preferably, Xaa is a helix promoting residue
      independently selected from the group consisting of Glu, Ala, Leu,
      Met, Gln, Lys, Arg, Val, Ile, Trp, Phe and Asp

<400> SEQUENCE: 3

Arg Gly Asp Leu Xaa Xaa Leu Xaa Xaa Xaa
1               5                   10

<210> SEQ ID NO 4
<211> LENGTH: 30
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (5, 6, 8..10)
<223> OTHER INFORMATION: Xaa is any residue
<220> FEATURE:
<221> NAME/KEY: misc_feature
<222> LOCATION: (5, 6, 8..10)
<223> OTHER INFORMATION: Preferably, Xaa is a helix promoting residue
<220> FEATURE:
<221> NAME/KEY: misc_feature
<222> LOCATION: (5, 6, 8..10)
<223> OTHER INFORMATION: Preferably, Xaa is a helix promoting residue
      independently selected from the group consisting of Glu, Ala, Leu,
      Met, Gln, Lys, Arg, Val, Ile, Trp, Phe and Asp
<220> FEATURE:
<221> NAME/KEY: misc_feature
<222> LOCATION: (11)..(30)
<223> OTHER INFORMATION: Any 19 Xaa's may be present or absent;
      represents a range of between 1 and 20 helix promoting residues

<400> SEQUENCE: 4

Arg Gly Asp Leu Xaa Xaa Leu Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
```

```
            20              25              30

<210> SEQ ID NO 5
<211> LENGTH: 80
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(35)
<223> OTHER INFORMATION: Any 34 Xaa's may be present or absent;
      represents a range of between 1 and 35 residues
<220> FEATURE:
<221> NAME/KEY: misc_feature
<222> LOCATION: (1)..(35)
<223> OTHER INFORMATION: Xaa is a residue which enhances the hydrophobic
      interactions with the helix defined from LXXL and also enhances
      the hammerhead RGD for binding
<220> FEATURE:
<221> NAME/KEY: misc_feature
<222> LOCATION: (40, 41, 43..45)
<223> OTHER INFORMATION: Xaa is any residue
<220> FEATURE:
<221> NAME/KEY: misc_feature
<222> LOCATION: (46)..(80)
<223> OTHER INFORMATION: Xaa is a helix promoting residue
<220> FEATURE:
<221> NAME/KEY: misc_feature
<222> LOCATION: (46)..(80)
<223> OTHER INFORMATION: Any 34 Xaa's may be present or absent;
      represents a range of between 1 and 35 residues

<400> SEQUENCE: 5

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Arg Gly Asp Leu Xaa Xaa Leu Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

<210> SEQ ID NO 6
<211> LENGTH: 20
<212> TYPE: PRT
<213> ORGANISM: Artificial sequence
<220> FEATURE:
<223> OTHER INFORMATION: Synthetic peptide: A20 LAP
<220> FEATURE:
<221> NAME/KEY: misc_feature
<222> LOCATION: (1)..(1)
<223> OTHER INFORMATION: Linked to Biotin-epsilonAhx in peptide B-A20LAP

<400> SEQUENCE: 6

Gly Phe Thr Thr Gly Arg Arg Gly Asp Leu Ala Thr Ile His Gly Met
1               5                   10                  15

Asn Arg Pro Phe
            20

<210> SEQ ID NO 7
<211> LENGTH: 20
<212> TYPE: PRT
<213> ORGANISM: Artificial sequence
<220> FEATURE:
<223> OTHER INFORMATION: Synthetic peptide: A20 FMDV-1
<220> FEATURE:
```

```
<221> NAME/KEY: misc_feature
<222> LOCATION: (1)..(1)
<223> OTHER INFORMATION: Linked to Biotin-epsilonAhx in peptide B-
      A20FMDV1

<400> SEQUENCE: 7

Tyr Thr Ala Ser Ala Arg Gly Asp Leu Ala His Le

<400> SEQUENCE: 11

Thr Gly Arg Arg Gly Asp Leu Ala Thr Ile
1               5                   10

<210> SEQ ID NO 12
<211> LENGTH: 12
<212> TYPE: PRT
<213> ORGANISM: Artificial sequence
<220> FEATURE:
<223> OTHER INFORMATION: Synthetic peptide: Peptide DD19

<400> SEQUENCE: 12

Val Pro Asn Leu Arg Gly Asp Leu Gln Val Leu Ala
1               5                   10

<210> SEQ ID NO 13
<211> LENGTH: 21
<212> TYPE: PRT
<213> ORGANISM: Artificial sequence
<220> FEATURE:
<223> OTHER INFORMATION: Synthetic peptide: P18-INK

<400> SEQUENCE: 13

Ser Ala Ala Ala Arg Gly Asp Leu Glu Gln Leu Thr Ser Leu Leu Gln
1               5                   10                  15

Asn Asn Val Asn Val
            20

<210> SEQ ID NO 14
<211> LENGTH: 22
<212> TYPE: PRT
<213> ORGANISM: Artificial sequence
<220> FEATURE:
<223> OTHER INFORMATION: Synthetic peptide: DBD1
<220> FEATURE:
<221> NAME/KEY: MISC_FEATURE
<222> LOCATION: (1)..(3)
<223> OTHER INFORMATION: D-Glu D-Tyr D-Lys tail
<220> FEATURE:
<221> NAME/KEY: MISC_FEATURE
<222> LOCATION: (1)..(1)
<223> OTHER INFORMATION: Linked to Biotin-epsilonAhx in peptide B-DBD1
<220> FEATURE:
<221> NAME/KEY: DISULFID
<222> LOCATION: (4)..(19)
<223> OTHER INFORMATION: Disulphide cyclised

<400> SEQUENCE: 14

Xaa Xaa Xaa Cys Pro Asn Leu Arg Gly Asp Leu Gln Val Leu Ala Gln
1               5                   10                  15

Lys Val Cys Arg Thr Lys
            20

<210> SEQ ID NO 15
<211> LENGTH: 22
<212> TYPE: PRT
<213> ORGANISM: Artificial sequence
<220> FEATURE:
<223> OTHER INFORMATION: Synthetic peptide: Ran
<220> FEATURE:
<221> NAME/KEY: MISC_FEATURE
<222> LOCATION: (1)..(3)
<223> OTHER INFORMATION: D-Glu D-Tyr D-Lys tail
<220> FEATURE:
<221> NAME/KEY: MISC_FEATURE
<222> LOCATION: (1)..(1)
<223> OTHER INFORMATION: Linked to Biotin-epsilonAhx in peptide B-Ran
<220> FEATURE:

```
<221> NAME/KEY: DISULFID
<222> LOCATION: (4)..(19)
<223> OTHER INFORMATION: Disulphide cyclised

<400> SEQUENCE: 15

Xaa Xaa Xaa Cys Lys Leu Val Gly Ala Leu Gln Pro Asp Asn Val Leu
1               5                   10                  15

Gln Arg Cys Arg Thr Lys
            20

<210> SEQ ID NO 16
<211> LENGTH: 20
<212> TYPE: PRT
<213> ORGANISM: Artificial sequence
<220> FEATURE:
<223> OTHER INFORMATION: Synthetic peptide: DBD2
<220> FEATURE:
<221> NAME/KEY: misc_feature
<222> LOCATION: (1)..(1)
<223> OTHER INFORMATION: Linked to Biotin-epsilonAhx in peptide B-DBD2
<220> FEATURE:
<221> NAME/KEY: DISULFID
<222> LOCATION: (1)..(20)
<223> OTHER INFORMATION: Disulphide cyclised

<400> SEQUENCE: 16

Cys Tyr Val Pro Asn Leu Arg Gly Asp Leu Gln Val Leu Ala Gln Lys
1               5                   10                  15

Val Ala Lys Cys
            20

<210> SEQ ID NO 17
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (5, 6, 8, 9)
<223> OTHER INFORMATION: Xaa is any residue
<220> FEATURE:
<221> NAME/KEY: misc_feature
<222> LOCATION: (10)..(11)
<223> OTHER INFORMATION: Contact residue

<400> SEQUENCE: 17

Arg Gly Asp Leu Xaa Xaa Leu Xaa Xaa Xaa Xaa
1               5                   10

<210> SEQ ID NO 18
<211> LENGTH: 7
<212> TYPE: PRT
<213> ORGANISM: Artificial sequence
<220> FEATURE:
<223> OTHER INFORMATION: Synthetic peptide: DD4

<400> SEQUENCE: 18

Gly Arg Arg Gly Asp Leu Ala
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic peptide: DD5

<400> SEQUENCE: 19
```

```
Phe Thr Thr Gly Arg Arg Gly Asp Leu
1               5

<210> SEQ ID NO 20
<211> LENGTH: 11
<212> TYPE: PRT
<213> ORGANISM: Artificial sequence
<220> FEATURE:
<223> OTHER INFORMATION: Synthetic peptide: DD6

<400> SEQUENCE: 20

Leu Arg Arg Gly Asp Arg Pro Ser Leu Arg Tyr
1               5                   10

<210> SEQ ID NO 21
<211> LENGTH: 9
<212> TYPE: PRT
<213> ORGANISM: Artificial sequence
<220> FEATURE:
<223> OTHER INFORMATION: Synthetic peptide: DD7

<400> SEQUENCE: 21

Leu Arg Arg Gly Asp Arg Pro Ser Leu
1               5

<210> SEQ ID NO 22
<211> LENGTH: 7
<212> TYPE: PRT
<213> ORGANISM: Artificial sequence
<220> FEATURE:
<223> OTHER INFORMATION: Synthetic peptide: DD8

<400> SEQUENCE: 22

Leu Arg Arg Gly Asp Arg Pro
1               5

<210> SEQ ID NO 23
<211> LENGTH: 11
<212> TYPE: PRT
<213> ORGANISM: Artificial sequence
<220> FEATURE:
<223> OTHER INFORMATION: Synthetic peptide: DD9

<400> SEQUENCE: 23

Gly Gly Leu Arg Arg Gly Asp Arg Pro Ser Leu
1               5                   10

<210> SEQ ID NO 24
<211> LENGTH: 9
<212> TYPE: PRT
<213> ORGANISM: Artificial sequence
<220> FEATURE:
<223> OTHER INFORMATION: Synthetic peptide: DD10

<400> SEQUENCE: 24

Gly Gly Leu Arg Arg Gly Asp Arg Pro
1               5

<210> SEQ ID NO 25
<211> LENGTH: 10
<212> TYPE: PRT
<213> ORGANISM: Artificial sequence
<220> FEATURE:
<223> OTHER INFORMATION: Synthetic peptide: DD11

<400> SEQUENCE: 25
```

Gly Leu Arg Arg Gly Asp Arg Pro Ser Leu
1               5                   10

<210> SEQ ID NO 26
<211> LENGTH: 7
<212> TYPE: PRT
<213> ORGANISM: Artificial sequence
<220> FEATURE:
<223> OTHER INFORMATION: Synthetic peptide: DD12

<400> SEQUENCE: 26

Arg Gly Asp Arg Pro Ser Leu
1               5

<210> SEQ ID NO 27
<211> LENGTH: 11
<212> TYPE: PRT
<213> ORGANISM: Artificial sequence
<220> FEATURE:
<223> OTHER INFORMATION: Synthetic peptide: DD13

<400> SEQUENCE: 27

Gly Gly Phe Arg Arg Gly Asp Arg Pro Ser Leu
1               5                   10

<210> SEQ ID NO 28
<211> LENGTH: 12
<212> TYPE: PRT
<213> ORGANISM: Artificial sequence
<220> FEATURE:
<223> OTHER INFORMATION: Synthetic peptide: DD14

<400> SEQUENCE: 28

Gly Ser Ile Tyr Asp Gly Tyr Tyr Val Phe Pro Tyr
1               5                   10

<210> SEQ ID NO 29
<211> LENGTH: 11
<212> TYPE: PRT
<213> ORGANISM: Artificial sequence
<220> FEATURE:
<223> OTHER INFORMATION: Synthetic peptide: DD15

<400> SEQUENCE: 29

Asn Ala Gly Arg Arg Gly Asp Leu Gly Ser Leu
1               5                   10

<210> SEQ ID NO 30
<211> LENGTH: 9
<212> TYPE: PRT
<213> ORGANISM: Artificial sequence
<220> FEATURE:
<223> OTHER INFORMATION: Synthetic peptide: DD16

<400> SEQUENCE: 30

Gly Arg Arg Gly Asp Leu Gly Ser Leu
1               5

<210> SEQ ID NO 31
<211> LENGTH: 10
<212> TYPE: PRT
<213> ORGANISM: Artificial sequence
<220> FEATURE:
<223> OTHER INFORMATION: Synthetic peptide: DD17

<400> SEQUENCE: 31

Asn Ala Gly Arg Arg Gly Asp Leu Gly Ser

```
<210> SEQ ID NO 32
<211> LENGTH: 8
<212> TYPE: PRT
<213> ORGANISM: Artificial sequence
<220> FEATURE:
<223> OTHER INFORMATION: Synthetic peptide: DD18

<400> SEQUENCE: 32

Asn Ala Gly Arg Arg Gly Asp Leu
1               5

<210> SEQ ID NO 33
<211> LENGTH: 20
<212> TYPE: PRT
<213> ORGANISM: Artificial sequence
<220> FEATURE:
<223> OTHER INFORMATION: Synthetic peptide: P_FMDV2

<400> SEQUENCE: 33

Val Pro Asn Leu Arg Gly Asp Leu Gln Val Leu Ala Gln Lys Val Ala
1               5                   10                  15

Arg Thr Leu Pro
            20

<210> SEQ ID NO 34
<211> LENGTH: 20
<212> TYPE: PRT
<213> ORGANISM: Artificial sequence
<220> FEATURE:
<223> OTHER INFORMATION: Synthetic peptide: P_18INK

<400> SEQUENCE: 34

Ser Ala Ala Ala Arg Gly Asp Leu Glu Gln Leu Thr Ser Leu Leu Gln
1               5                   10                  15

Asn Asn Val Asn
            20

<210> SEQ ID NO 35
<211> LENGTH: 20
<212> TYPE: PRT
<213> ORGANISM: Artificial sequence
<220> FEATURE:
<223> OTHER INFORMATION: Synthetic peptide: P_FMDV2-INK

<400> SEQUENCE: 35

Val Pro Asn Leu Arg Gly Asp Leu Gln Val Leu Thr Ser Leu Leu Gln
1               5                   10                  15

Asn Asn Val Asn
            20

<210> SEQ ID NO 36
<211> LENGTH: 20
<212> TYPE: PRT
<213> ORGANISM: Artificial sequence
<220> FEATURE:
<223> OTHER INFORMATION: Synthetic peptide: P_INK-FMDV2

<400> SEQUENCE: 36

Ser Ala Ala Ala Arg Gly Asp Leu Glu Gln Leu Ala Gln Lys Val Ala
1               5                   10                  15

Arg Thr Leu Pro
            20
```

```
<210> SEQ ID NO 37
<211> LENGTH: 20
<212> TYPE: PRT
<213> ORGANISM: Artificial sequence
<220> FEATURE:
<223> OTHER INFORMATION: Synthetic peptide: P_INK-FMDV2-X

<400> SEQUENCE: 37

Ser Ala Ala Ala Arg Gly Asp Leu Glu Gln Le

```
<220> FEATURE:
<221> NAME/KEY: misc_feature
<222> LOCATION: (1)..(1)
<223> OTHER INFORMATION: Linked to Biotin-epsilonAhx

<400> SEQUENCE: 41

Arg Gln Leu Asn Val Asp Ala Leu Asn Val Ala Gly Val Arg Ala Leu
1               5                   10                  15

Lys Pro Thr Gln
            20
```